(12) United States Patent
Bredesen et al.

(10) Patent No.: US 7,544,855 B2
(45) Date of Patent: Jun. 9, 2009

(54) TRANSGENIC MOUSE WHOSE GENOME COMPRISES AN APP HAVING A MUTATION AT AMINO ACID 664

(75) Inventors: Dale E. Bredesen, Novato, CA (US); Veronica Galvan, Novato, CA (US)

(73) Assignee: Buck Institute, Novato, CA (US)

( * ) Notice: Subject to any disclaimer, the term of this patent is extended or adjusted under 35 U.S.C. 154(b) by 214 days.

(21) Appl. No.: 10/830,713

(22) Filed: Apr. 23, 2004

(65) Prior Publication Data
US 2005/0241008 A1    Oct. 27, 2005

(51) Int. Cl.
*A01K 67/027* (2006.01)
*A01K 67/00* (2006.01)
*G01N 33/00* (2006.01)

(52) U.S. Cl. ............. 800/18; 800/3; 800/8; 800/14
(58) Field of Classification Search ............ 800/3, 800/8, 14, 18
See application file for complete search history.

(56) References Cited

U.S. PATENT DOCUMENTS

| | | | |
|---|---|---|---|
| 4,046,722 | A | 9/1977 | Rowland |
| 4,631,190 | A | 12/1986 | Shen et al. |
| 4,701,521 | A | 10/1987 | Ryser et al. |
| 4,847,240 | A | 7/1989 | Ryser et al. |
| 5,144,011 | A | 9/1992 | Shen et al. |
| 5,149,796 | A | 9/1992 | Rossi et al. |
| 5,176,996 | A | 1/1993 | Hogan et al. |
| 5,222,982 | A | 6/1993 | Ommaya |
| 5,225,337 | A | 7/1993 | Robertson et al. |
| 5,225,347 | A | 7/1993 | Goldberg et al. |
| 5,246,921 | A | 9/1993 | Reddy et al. |
| 5,256,775 | A | 10/1993 | Froehler |
| 5,264,564 | A | 11/1993 | Matteucci |
| 5,268,164 | A | 12/1993 | Kozarich et al. |
| 5,387,742 | A | 2/1995 | Cordell |
| 5,455,169 | A | 10/1995 | Mullan |
| 5,795,963 | A | 8/1998 | Mullan |
| 5,877,015 | A | 3/1999 | Hardy et al. |
| 6,005,004 | A | 12/1999 | Katz et al. |
| 6,051,684 | A | 4/2000 | McDonlad et al. |
| 6,300,540 | B1 | 10/2001 | Hardy et al. |
| 6,689,784 | B2 | 2/2004 | Bebbington et al. |
| 6,818,448 | B2 | 11/2004 | Mullan |
| 2004/0192889 | A1 | 9/2004 | Bredesen |

FOREIGN PATENT DOCUMENTS

| | | |
|---|---|---|
| WO | WO 88/09810 | 12/1988 |
| WO | WO 89/01034 | 11/1989 |
| WO | WO 93/09236 | 5/1993 |
| WO | WO 98/15828 A1 | 4/1998 |
| WO | WO 98/15828 C1 | 4/1998 |
| WO | WO 02/092788 A2 | 11/2002 |
| WO | WO 02/092788 A3 | 11/2002 |

OTHER PUBLICATIONS

Houdebine LM, The methods to generate transgenic animals and to control transgene expression, 2002, J. of Biotechnology, vol. 98, pp. 145-160.*
Smith KR, Gene transfer in higher animals: theoretical considerations and key concepts, J. of Biotechnology, vol. 99, pp. 1-22.*
Ristevski S, Making better transgenic models, 2005, Molecular Biotechnology, vol. 29, pp. 153-163.*
Montoliu L, Gene transfer strategies in animal transgenesis, 2002, Cloning and Stem Cells, vol. 4, pp. 39-46.*
Echeverria et al., Rat transgenic models with a phenotype of intracellular Abeta accumulation in hippocampus and cortexJ Alzheimers Dis. Jun. 2004;6(3):209-19.*
Yang T., 2004, Am J Physiol Renal Physiol, vol. 288, pp. F1125-F1132.*
Dansky HM, 1999, Arterioscler Thromb Vasc Biol, vol. 19, pp. 1960-1968.*
Crabbe et al., 1999, Science, vol. 284, pp. 1670-1672.*
Dodart, J. C. et al., Neuroanatomical Abnormalities in Bahaviorally Characterized APP$^{V/1/F}$ Transgenic Mice, Neurobiol Dis 7:71-85 (2000).
Galvan et al., Caspase cleavage of members of the amyloid precursor family of proteins, J Neurochem 82:283-94 (2002).
Gautier et al., α-DNA IV: α-anomeric and β-anomeric tetrathymidylates covalently linked to intercalating oxazoloyridpyridocarbazole. Synthesis, physicochemical properties and poly (rA) binding, *Nucl. Acids Res.* 15:6625-6641 (1987).

(Continued)

*Primary Examiner*—David Montanari
(74) *Attorney, Agent, or Firm*—Morrison & Foerster LLP

(57) ABSTRACT

In accordance with the present invention, it is demonstrated that selected mutations such as an Asp->Ala (D664A) mutation in APP (which prevents cleavage at the caspase cleavage site) prevent both hippocampal synaptic loss and dentate gyral atrophy, even though such mutations do not interfere with the production of Aβ or the formation of amyloid plaques in a transgenic model of Alzheimer's disease. Accordingly, in view of this finding, methods have been developed for the identification of agents which block cleavage at Asp664 of APP, including transgenic animals which are useful for such purpose, as well as methods for the use thereof for the treatment of neurodegenerative diseases.

11 Claims, 5 Drawing Sheets

OTHER PUBLICATIONS

Gervais et al. Involvement of Caspases in Proteolytic Cleavage of Alzheimer's Amyloid-β Precursor Protein and Amyloidogenic Aβ Peptide Formation, Cell, 97:395-406 (1999).

Gonzalez-Lima et al., Reduced corpus callosum, fornix and hippocampus in PDAPP transgenic mouse model of Alzheimer's disease. Clinical Neuroscience and Neuropathology, 12(118):2375-2379 (2001).

Hsia, A. Y. et al., Plaque-independent disruption of neural circuits in Alzheimer's disease mouse models, *Proc Natl Acad Sci USA* 96:3228-33 (1999).

Holtzman et al., Apolipoprotein E isoform-dependent amyloid deposition and neuritic degeneration in a mouse model of Alzheimer's disease, Proc. Natl. Adad. Sci., 97(6):2892-2897 (2000).

Inoue et al., Sequence-dependent hydrolysis of RNA using modified oligonucleotide splints and Rnase H, FEBS Lett. 215:327-330 (1987).

Inoue et al., Synthesis and hybridization studies on two complementary nona(2'-O-methyl)ribonucleotides, *Nucl. Acids Res.* 15:6131-6148 (1987).

Jin, K. et al., Increased hippocampal neurogenesis in Alzheimer's disease, Proc. Natl. Acad. Sci. USA 101:343-7 (2004).

Lemaitre et al., Specific antiviral activity of a poly(L-lysine)-conjugated oligodeoxyribonucleotide sequence complementary to vesicular stomatitis virus N protein mRNA initiation site, *Proc. Natl. Acad. Sci.* USA 84:648-652 (1987).

Letsinger et al., Cholesteryl-conjugated oligonucleotides: Synthesis, properties, and activity as inhibitors of replication of human immunodeficiency virus in cell culture, *Proc. Natl. Acad. Sci.* U.S.A. 86:6553-6556 (1989).

Li, Y. et al., Targeted expression of human CuZn superoxide dismutase gene in mouse central nervous system, J Neurosci Methods 89, 49-55 (1999).

Lu et al., Amyloid β Protein Toxicity Mediated by the Formation of Amyloid-β Protein Precursor Complexes, Ann. Neurol., 54:781-789 (2003).

McManus, et al., Gene Silencing in Mammals by Small Interfering RNAs, *Nature Reviews Genetics* 3:737 (2002).

Miller, A. D., "Human gene therapy comes of age," *Nature* 357:455-460 (1992).

Mucke, et al., "High-Level Neuronal Expression of Aβ$_{1-42}$ in Wild-Type Human Amyloid Protein Precursor Transgenic Mice: Synaptotoxicity without Plaque Formation," The Journal of Neuroscience, 20(11):4050-4058 (2000).

Rubin, Emmanuel, Editor, "The Nervous System," Pathology, 3rd ed., pp. 1492-1496 (1999).

Rubin, Emmanuel, Editor, "Amyloidosis," Pathology, 3rd ed., p. 1226 (1999).

Perreault, et al., Mixed deoxyribo- and ribo- oligonucleotides with catalytic activity, *Nature*, 344:565-567 (1990).

Redwine, J. M. et al., Dentate gyrus volume is reduced beore onset of plaque formation in PDAPP mice: A magnetic resonance microscopy and stereologic analysis, Proc Natl Acad Sci USA 100:1381-6 (2003).

Selkoe, D. J., Alzheimer's Disease Is a Synaptic Failure, Science, 298:789-791 (2002).

Soriano et al., The amyloidogenic pathway of Amyloid Precursor Protein (APP) Is Independent of Its Ceavage by Caspaces, J. Biol. Chem., 276(31):29045-29050 (2001).

Van der Krol et al., Modulation of Eukaryotic Gene Expression by Complementary RNA or DNA Sequences, BioTechniques 6:958-976 (1988).

Weggen, et al, A subset of NSAIDs lower amyloidogenic Aβ42 independently of cyclooxygenase activity, Nature 414:212-6 (2001).

Wyss-Coray, T. et al., Amyloidogenic role of cytokine TGF-β1 in transgenic mice and in Alzheimer's disease,-Nature 389:603-6 (1997).

Zon, G., Oligonucleotide Analogues as Potential Chemotherapeutic Agents, *Pharm. Res.* 5:539-549 (1988).

Anonymous. (e-pub. Mar. 7, 2008). "Memory Loss in Hyperactive State With Alzheimer's Study Suggests Brains of Patients Get Stuck in Memory-Deletion Mode," *U.S. News & Word Report*, located at http://health.usnews.com/usnews/health/healthday/080307/memory-loss-in-hyperactive-state-with-alzheimers.htm>, last visited on Mar. 24, 2008, two pages.

Banks, W.A. et al. (1992). "Bidirectional Passage of Peptides Across the Blood-Brain Barrier," Chapter 21 in *Circumventricular Organs and Brain Fluid Environment: Molecular and Functional Aspects*, Ermisch, A. et al. eds., Elsevier Science Publishers B.V.: Amsterdam, pp. 139-148.

Banwait, S. (Feb. 2008). "C-Terminal Cleavage of the Amyloid-β Protein Precursor at Asp664: A Switch Associated with Alzheimer's Disease," *J. Alzheimers Dis.* 13(1):1-16.

Barnes, N.Y. et al. (Aug. 1, 1998). "Increased Production of Amyloid Precursor Protein Provides a Substrate for Caspase-3 in Dying Motoneurons," *J. Neurosci.* 18(15):5869-5880.

Bobo, R.H. et al. (Mar. 1994). "Convection-Enhanced Delivery of Macromolecules in the Brain," *Proc. Natl. Acad. Sci. USA* 91: 2076-2080.

Bredesen, D.E. (Dec. 1995). "Neural Apoptosis," *Ann. Neurol.* 38(6):839-851.

Bredesen, D.E. et al. (May 1998). "p75$^{NTR}$ and the Concept of Cellular Dependence: Seeing How the Other Half Die," *Cell Death Diff.* 5(5):365-371.

Brinster, R.L. et al. (Mar. 4, 1982). "Regulation of Metallothionein-Thymidine Kinase Fusion Plasmids Injected into Mouse Eggs," *Nature* 296(5852):39-42.

Broadwell, R.D. (1989). "Transcytosis of Macromolecules Through the Blood-Brain Barrier: a Cell Biological Perspective and Critical Appraisal," *Acta Neuropathol.* 79(2):117-128.

Capecchi, M.R. (Nov. 1980). "High Efficiency Transformation by Direct Microinjection of DNA into Cultured Mammalian Cells," *Cell* 22(1)(Part 2):479-488.

Caporaso, G.L. et al. (May 1994). "Morphologic and Biochemical Analysis of the Intracellular Trafficking of the Alzheimer β/A4 Amyloid Precursor Protein," *J. Neurosci.* 14(5):3122-3138.

Chan, S.L. et al. (Aug. 1, 1999). "Evidence for Caspase-Mediated Cleavage of AMPA Receptor Subunits in Neuronal Apoptosis and Alzheimer's Disease," *J. Neurosci. Res.* 57(3):315-323.

Chen, C. et al. (Aug. 1987). "High-Efficiency Transformation of Mammalian Cells by Plasmid DNA," *Mol. Cell Biol.* 7(8):2745-2752.

Cheng, Y. (May 1998). "Caspase Inhibitor Affords Neuroprotection with Delayed Administration in a Rat Model of Neonatal Hypoxic-Ischemic Brain Injury," *J. Clin. Invest.* 101(9):1992-1999.

Chu, G. et al. (1987). "Electroporation for the Efficient Transfection of Mammalian Cells with DNA," *Nucleic Acids Res.* 15(3):1311-1326.

Ciliberto, G. et al. (Jun. 1985). "Cell-Specific Expression of a Transfected Human α$_1$-Antitrypsin Gene," *Cell* 41:531-540.

Clontech (Jul. 1996). "Tet Expression Systems and Cell Lines: Mammalian Cell Culture Systems for Tightly Regulated, High-Level Gene Expression," 9(3):2-5.

Cotman, C.W. et al. (Feb. 1995). "A Potential Role for Apoptosis in Neurodegeneration and Alzheimer's Disease," *Mol. Neurobiol.* 10(1):19-45.

Cotman, C.W. (Jan.-Feb. 1998). "Apoptosis Decision Cascades and Neuronal Degeneration in Alzheimer's Disease," *Neurobiol. Aging* 19(1S):S29-S32.

Cowan, C.M. et al. (Sep. 15, 2001). "Caspases 3 and 9 Send a Pro-Apoptotic Signal From Synapse to Cell Body in Olfactory Receptor Neurons," *J. Neurosci.* 21(18): 7099-7109.

Curiel, D.T. et al. (1992). "Gene Transfer to Respiratory Epithelial Cells via the Receptor-mediated Endocytosis Pathway," *Am. J. Respir. Cell. Mol. Biol.* 6:247-252.

Delort, J.P. et al. (May 1, 1996). "TAXI/UAS: A Molecular Switch to Control Expression of Genes In Vivo," *Hum. Gene Ther.* 7(7):809-820.

Dovey, H.F. et al. (Jan. 2001). "Functional Gamma-Secretase Inhibitors Reduce Beta-Amyloid Peptide Levels in Brain," *J. Neurochem.* 76(1):173-181.

Dumanchin-Njock, C. et al. (Sep. 2001). "The Caspase-Derived C-Terminal Fragment of βAPP Induces Caspase-Independent Toxicity And Triggers Selective Increase of Aβ42 in Mammalian Cells," *J. Neurochem.* 78(5):1153-1161.

Ellerby, L.M. et al. (Jan. 26, 1999). "Kennedy's Disease: Caspase Cleavage of the Androgen Receptor Is a Crucial Event in Cytotoxicity," *J. Neurochem.* 72(1):185-195.

Felgner, P.L. et al. (Nov. 1987). "Lipofection: A Highly Efficient, Lipid-Mediated DNA-Transfection Procedure," *Proc. Natl. Acad. Sci. USA* 84:7413-7417.

Felgner, P.L. et al. (Jan. 26, 1989). "Cationic Liposome-Mediated Transfection," *Nature* 337(6205):387-388.

Frain, M. et al. (Mar. 1990). "Binding of a Liver-Specific Factor to the Human Albumin Gene Promoter and Enhancer," *Mol. Cell. Biol.* 10(3):991-999.

Fukuchi, K. et al. (May 14, 1993). "Selective Neurotoxicity of COOH-Terminal Fragments of the β-Amyloid Precursor Protein," *Neurosci. Lett.* 154(1,2):145-148.

Galvan, V. (May 2, 2006). "Reversal of Alzheimer's-like Pathology and Behavior in Human APP Transgenic Mice by Mutation of Asp664," *Proc. Natl. Acad. Sci. USA* 103(18):7130-7135.

Glick, B.R. et al. (Feb. 1987). "Factors Affecting the Expression of Foreign Proteins in *Escherichia coli*," *J. Ind. Microbiol.* 1(5):277-282.

Green, M. et al. (Oct. 1980). "Transcripts of the Adeno-Associated Virus Genome: Mapping of the Major RNAs," *J. Virol.* 36(1):79-92.

Hanahan, D. (May 9, 1985). "Heritable Formation of Pancreatic β-Cell Tumours in Transgenic Mice Expressing Recombinant Insulin/Simian Virus 40 Oncogenes," *Nature* 315(6015):115-122.

Hennighausen, L. et al. (1986). "Nuclear Factor 1 Interacts with Five DNA Elements in the Promoter Region of the Human Cytomegalovirus Major Immediate Early Gene," *EMBO J.* 5(6):1367-1371.

Hileman, M.R. et al. (1997). "A Cytoplasmic Peptide of the Neurotrophin Receptor p75NTR: Induction of Apoptosis and NMR Determined Helical Conformation," *FEBS Lett.* 415:145-154.

Hwang, D.Y. (Jun. 2002). "Alterations in Behavior, Amyloid β-42, Caspase-3, and Cox-2 in Mutant PS2 Transgenic Mouse Model of Alzheimer's Disease," *FASEB J.* 16(8):805-813.

International Search Report and Written Opinion mailed on Jun. 27, 2006, for International Patent Application No. PCT/US/05/13761, filed on Apr. 4, 2005, five pages.

International Search Report mailed on Jun. 27, 2006, for International Patent Application No. PCT/US/05/13761, filed Apr. 4, 2005, two pages.

Kelsey, G.D. et al. (Apr. 1987). "Species- and Tissue-Specific Expression of Human $\alpha_1$-Antitrypsin in Transgenic Mice," *Genes Dev.* 1(2):161-171.

Koo, E.H. et al. (Jul. 1, 1994). "Evidence That Production and Release of Amyloid β-Protein Involves the Endocytic Pathway," *J. Biol. Chem.* 269(26):17386-17389.

Krajewski, S. et al. (May 1999). "Release of Caspase-9 from Mitochondria during Neuronal Apoptosis and Cerebral Ischemia," *Proc. Natl. Acad. Sci. USA* 96:5752-5757.

Kyöstio, S.R. et al. (Oct. 1991). "*Erwinia carotovora* subsp. *caratovora* Extracellular Protease: Characterization and Nucleotide Sequence of the Gene," *J. Bacteriol.* 173(20):6537-6546.

Laferla, F.M. et al. (Jan. 1995). "The Alzheimer's Aβ Peptide Induces Neurodegeneration and Apoptotic Cell Death in Transgenic Mice," *Nature Genet.* 9(1):21-30.

Lang, D. et al. (1992). "Analysis of Proteins Binding to the Proximal Promoter Region of the Human Cytomegalovirus IE-1/2 Enhancer/Promoter Reveals Both Consensus and Aberrant Recognition Sequences for Transcription Factors Sp1 and CREB," *Nucleic Acids Res.* 20(13):3287-3295.

Leblanc, A. et al. (Aug. 13, 1999). "Caspase-6 Role in Apoptosis of Human Neurons, Amyloidogenesis, and Alzheimer's Disease," *J. Biol. Chem.* 274(33):23426-23436.

Leder, A. et al. (May 23, 1986). "Consequences of Widespread Deregulation of the c-*myc* Gene in Transgenic Mice: Multiple Neoplasms and Normal Development," *Cell* 45(4):485-495.

Lehner, R. et al. (Nov. 1991). "Comparative Sequence Analysis of Human Cytomegalovirus Strains," *J. Clin. Microbiol.* 29(11):2494-2502.

Lu, D.C. et al. (Apr. 2000). "A Second Cytotoxic Proteolytic Peptide Derived From Amyloid β-Protein Precursor," *Nat. Med.* 6(4):397-404.

Lyckman, A.W. et al. (May 1, 1998). "Post-translational Processing and Turnover Kinetics of Presynaptically Targeted Amyloid Precursor Superfamily Proteins in the Central Nervous System," *J. Biol. Client.* 273(18):11100-11106.

MacDonald, R.J. (Jan.-Feb. 1987). "Expression of the Pancreatic Elastase I Gene in Transgenic Mice," *Hepatology* 7(1 Suppl.):42S-51S.

Marquez-Sterling, N.R. et al. (Jan. 1, 1997). "Trafficking of Cell-Surface β-Amyloid Precursor Protein: Evidence that a Sorting Intermediate Participates in Synaptic Vesicle Recycling," *J. Neurosci.* 17(1):140-151.

Masliah, E. (1998). "Mechanisms of Synaptic Pathology in Alzheimer's Disease," In *Ageing and Dementia*, Jellinger, K. et al., eds., Springer-Verlag: Wien, Austria, pp. 147-158.

Masliah, E. et al. (Jan. 9, 2001). "Altered Expression of Synaptic Proteins Occurs Early During Progression of Alzheimer's Disease," *Neurology* 56(1):127-129.

Mason, A.J. et al. (Dec. 12, 1986). "The Hypogonadal Mouse: Reproductive Functions Restored by Gene Therapy," *Science* 234(4772):1372-1378.

Mattson, M.P. et al. (Oct. 5, 1998). "Amyloid β-peptide Induces Apoptosis-Related Events in Synapses and Dendrites," *Brain Res.* 807(1,2):167-176.

McPhie, D.L. et al. (Oct. 3, 1997) "Neuronal Expression of β-Amyloid Precursor Protein Alzheimer Mutations Causes Intracellular Accumulation of a C-terminal Fragment Containing Both the Amyloid β and Cytoplasmic Domains," *J. Biol. Chem.* 272(40):24743-24746.

Mehlen, P. et al. (Oct. 22, 1998). "The DCC Gene Product Induces Apoptosis by a Mechanism Requiring Receptor Proteolysis," *Nature* 395:801-804.

Milligan, C.E. (Apr. 2000). "Caspase Cleavage of APP Results in a Cytotoxic Proteolytic Peptide," *Nat. Med.* 6(4):385-386.

Mochizuki, H. (Oct. 2002) "Adeno-Associated Virus-Mediated Antiapoptotic Gene Delivery: In Vivo Gene Therapy for Neurological Disorders," *Methods* 28(2):248-252.

Mulligan, R.C. (May 14, 1993). "The Basic Science of Gene Therapy," *Science* 260:926-932.

Ommaya, A.K. (1984). "Implantable Devices for Chronic Access and Drug Delivery to the Central Nervous System," *Cancer Drug Deliv.* 1(2):169-179.

Oster-Granite, M.L. et al. (Nov. 1, 1996). "Age-Dependent Neuronal and Synaptic Degeneration in Mice Transgenic for the C Terminus of the Amyloid Precursor Protein," *J. Neurosci.* 16(21):6732-6741.

Paliga, K. et al. (Dec. 1, 1997). "Human Amyloid Precursor-like Protein 1 cDNA Cloning, Ectopic Expression in COS-7 Cells and Identification of Soluble Forms in the Cerebrospinal Fluid," *Eur. J. Biochem.* 250(2):354-363.

Pardridge, W.M. et al. (Nov. 1990). "Evaluation of Cationized Rat Albumin as a Potential Blood-Brain Barrier Drug Transport Vector," *J. Pharmacol. Exp. Ther.* 255(2):893-899.

Pardridge, W.M. (1991). "Blood-Brain Barrier Transport of Glucose, Free Fatty Acids, and Ketone Bodies," in *Fuel Homeostasis and the Nervous System*, Vranic, M. et al., Plenum Press: New York, pp. 43-53.

Passer, B. et al. (2000). "Generation of an Apoptotic Intracellular Peptide by γ-Secretase Cleavage of Alzheimer's Amyloid β Protein Precursor," *J. Alzheimer's Dis.* 2:289-301.

Pellegrini, L. et al. (Jul. 23, 1999). "Alternative, Non-secretase Processing of Alzheimer's β-Amyloid Precursor Protein during Apoptosis by Caspase-6 and -8," *J. Biol. Chem.* 274(30):21011-21016.

Pinkert, C.A. et al. (1987). "An Albumin Enhancer Located 10 Kb Upstream Functions Along with its Promoter to Direct Efficient, Liver-Specific Expression in Transgenic Mice," *Genes and Devel.* 1:268-276.

Pinnix, I. et al. (Jan. 5, 2001). "A Novel γ-Secretase Assay Based on Detection of the Putative C-terminal Fragment-γ of Amyloid β Protein Precursor," *J. Biol. Chem.* 276(1):481-487.

Rabizadeh, S. et al. (Jul. 16, 1993). "Induction of Apoptosis by the Low-Affinity NGF Receptor," *Science* 261:345-348.

Readhead, C. et al. (Feb. 27, 1987). "Expression of a Myelin Basic Protein Gene in Transgenic Shiverer Mice: Correction of the Dysmyelinating Phenotype," *Cell* 48(4):703-712.

Saganich, M.J. (Dec. 27, 2006). "Deficits in Synaptic Transmission and Learning in Amyloid Precursor Protein (APP) Transgenic Mice Require C-Terminal Cleavage of APP," *J. Neurosci.* 26(52):13428-13436.

Salvesen, G.S. et al. (Nov. 14, 1997). "Caspases: Intracellular Signaling by Proteolysis," *Cell* 91:443-446.

Schrewe, H. et al. (Jun. 1990). "Cloning of the Complete Gene for Carcinoembryonic Antigen: Analysis of Its Promoter Indicates a Region Conveying Cell Type-Specific Expression," *Mol. Cell Biol.* 10(6):2738-2748.

Schwarze, S.R. et al. (Jul. 2000). "Protein Transduction: Unrestricted Delivery into All Cells?" *Trends Cell Biol.* 10(7):290-295.

Selkoe, D.J. (Nov. 1998). "The Cell Biology of β-amyloid Precursor Protein and Presenilin in Alzheimer's Disease," *Trends Cell Biol.* 8:447-453.

Selznick, L.A. et al. (Sep. 1999). "In Situ Immunodetection of Neuronal Caspase-3 Activation in Alzheimer Disease," *J. Neuropathol. Exp. Neurol.* 58(9):1020-1026.

Sisodia, S.S. et al. (Jul. 1993). "Identification and Transport of Full-Length Amyloid Precursor Proteins in Rat Peripheral Nervous System," *J. Neurosci.* 13(7):3136-3142.

Sopher, B.L. et al. (Oct. 1994). "Cytotoxicity Mediated by Conditional Expression of a Carboxyl-Terminal Derivative of the β-amyloid Precursor Protein," *Mol. Brain Res.* 26(1/2):207-217.

Sperandio, S. et al. (Dec. 19, 2000). "An Alternative, Nonapoptotic Form of Programmed Cell Death," *Proc. Natl. Acad. Sci. USA* 97(26):14376-14381.

Sperandio, S. et al. (Dec. 19, 2000). "An Alternative, Nonapoptotic Form of Programmed Cell Death," *Proc. Natl. Acad. Sci. USA,* Supplemental Figures, located at <http://www.pnas.org/cgi/content/full/97/26/14376/DC1>, last visited on Jan. 4, 2008, six pages.

Sprecher, C.A. et al. (May 4, 1993). "Molecular Cloning of the cDNA for a Human Amyloid Precursor Protein Homolog: Evidence for a Multigene Family," *Biochemistry* 32(17):4481-4486.

Srivastava, A. et al. (Feb. 1983). "Nucleotide Sequence and Organization of the Adeno-Associated Virus 2 Genome," *J. Virol.* 45(2):555-564.

Stadelmann, C. et al. (Nov. 1999). "Activation of Caspase-3 in Single Neurons and Autophagic Granules of Granulovacuolar Degeneration in Alzheimer's Disease: Evidence for Apoptotic Cell Death," *Am. J. Pathol.* 155(5):1459-1466.

Stennicke, H.R. et al. (Oct. 16, 1998). "Pro-caspase-3 Is a Major Physiologic Target of Caspase-8," *J. Biol. Chem.* 273(42):27084-27090.

Swift, G.H. et al. (Oct. 1984). "Tissue-Specific Expression of the Rat Pancreatic Elastase I Gene in Transgenic Mice," *Cell* 38(3):639-646.

Terry, R.D. et al. (Oct. 1991). "Physical Basis of Cognitive Alterations in Alzheimer's Disease: Synapse Loss Is the Major Correlate of Cognitive Impairment," *Ann. Neurol.* 30(4):572-580.

Thornberry, N.A. et al. (Aug. 28, 1998). "Caspases: Enemies Within," *Science* 281:1312-1316.

Wagner, M.J. et al. (Mar. 1981). Nucleotide Sequence of the Thymidine Kinase Gene of Herpes Simplex Virus Type 1, *Proc. Natl. Acad. Sci. USA* 78(3):1441-1445.

Wagner, R. (Nov. 24, 1994). "Gene Inhibition Using Antisense Oligodeoxynucleotides," *Nature* 372(6504):333-335.

Weidemann, A. et al. (Feb. 26, 1999). "Proteolytic Processing of the Alzheimer's Disease Amyloid Precursor Protein within Its Cytoplasmic Domain by Caspase-like Proteases," *J. Biol. Chem.* 274(9):5823-5829.

Wolf, B.B. et al. (Sep. 1, 1999). "Calpain Functions in a Caspase-Independent Manner to Promote Apoptosis-Like Events During Platelet Activation," *Blood* 94(5):1683-1692.

Yang, F. et al. (Feb. 1998). "Antibody to Caspase-Cleaved Actin Detects Apoptosis in Differentiated Neuroblastoma and Plaque-Associated Neurons and Microglia in Alzheimer's Disease," *Am. J. Pathol.* 152(2):379-389.

Yang, N-S. et al. (Dec. 1990). "In Vivo and In Vitro Gene Transfer to Mammalian Somatic Cell by Particle Bombardment," *Proc. Natl. Acad. Sci. USA* 87:9568-9572.

Yankner, B.A. et al. (Jul. 28, 1989). "Neurotoxicity of a Fragment of the Amyloid Precursor Associated with Alzheimer's Disease," *Science* 245:417-420.

Yankner, B.A. (May 1996). "Mechanisms of Neuronal Degeneration in Alzheimer's Disease," *Neuron* 16:921-932.

Yuan, J. et al. (Oct. 12, 2000). "Apoptosis in the Nervous System," *Nature* 407:802-809.

Hwang et al., Alterations in behavior, amyloid β-42, caspase-3, and Cox-2 in mutant PS2 transgenic mouse model of Alzheimer's disease. FASEB J., 16:805-813, 2002.

Mochizuki et al., Adeno-associated virus-mediated antiapoptotic gene delivery: in vivo gene therapy for neurological disorders. Methods, 28:248-252, 2002.

\* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
ggtgagtttg taagtgatgc c                                         21

<210> SEQ ID NO 2
<211> LENGTH: 20
<212> TYPE: DNA
<213> ORGANISM: Artificial Sequence
<220> FEATURE:

```
<223> OTHER INFORMATION: Description of Artificial Sequence: Primer

<400> SEQUENCE: 2
tcttcttctt ccacctcagc                                              20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
caggccactg ggaggaaaaa tg                                           22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
accttctgtc atgtggaggt cc                                           22
```

TRANSGENIC MOUSE WHOSE GENOME COMPRISES AN APP HAVING A MUTATION AT AMINO ACID 664

FIELD OF THE INVENTION

The present invention relates to non-human transgenic models of Alzheimer's disease, and uses therefore, including methods for identifying compounds useful for the treatment of Alzheimer's, methods of treatment using such compounds, and the like.

BACKGROUND OF THE INVENTION

Alzheimer's disease (AD), the most common dementing disorder, is characterized by senile plaques, neurofibrillary tangles, and loss of synapses and neurons in the brain. The predominant proteinaceous component of the senile plaques is β-amyloid peptide (Aβ), which is produced by proteolytic cleavage of its precursor, the β-amyloid precursor protein (APP). The amyloid hypothesis states that Aβ initiates the cascade of events that results in AD. The precise mechanism of amyloid toxicity is unclear, but evidence has been accumulating that the synapse is an early vulnerable site for Aβ damage (see, for example, Selkoe, D. J. in Science 298:789-91(2002)). Consistent with this idea, some APP transgenic mice with high levels of Aβ in the brain show synapse loss, behavioral changes, and reductions in synaptic transmission prior to the formation of senile plaques (see Hsia, A. Y. et al. in Proc Natl Acad Sci USA 96:3228-33 (1999) and Mucke et al., in J. Neurosci. 20:4050-8 (2000)). Recently, it has been shown that APP is also cleaved at Asp664 (APP695 numbering) by caspases, the cysteine proteases that mediate apoptosis (see Gervais, F. G. et al. in Cell 97:395-406 (1999) and Lu, D. C. et al. in Nat Med 6:397-404 (2000)). Such processing liberates a cytotoxic carboxyterminal peptide, APP-C31; however, the role (if any) that caspase processing of APP may play in AD is unknown. This generation of a cytotoxic peptide following intracytoplasmic cleavage by caspases is similar to what has been shown to occur for dependence receptors such as DCC (deleted in colorectal cancer), RET (rearranged during transfection) and UNC5H1-3 (uncoordinated gene 5 homologues 1-3), suggesting that APP may function as a dependence receptor (Bredesen et al., Physiological Reviews, in press 2004).

Accordingly, development of transgenic models that allow investigation into the role that proteases, such as caspases, play in the development of such neurodegenerative diseases as Alzheimer's disease, would be of great interest. In addition, the availability of such transgenic models would facilitate development of new treatments for neurodegenerative diseases.

SUMMARY OF THE INVENTION

In accordance with the present invention, it is demonstrated that selected mutations, such as an Asp->Ala (D664A) mutation in APP (which prevents cleavage at the caspase cleavage site), prevent both hippocampal synaptic loss and dentate gyral atrophy, even though such mutations do not interfere with the production of Aβ or the formation of amyloid plaques in a transgenic model of Alzheimer's disease.

Accordingly, in view of this finding, methods have been developed for the identification of agents which block cleavage at Asp664 of APP, including transgenic animals which are useful for such purpose, as well as methods for the use thereof for the treatment of neurodegenerative diseases. Early intervention in the development of neurodegenerative diseases such as Alzheimer's disease will facilitate recovery of synaptic function, and reduce the loss of neuronal networks, a hallmark of advanced stages of neurodegenerative disease.

BRIEF DESCRIPTION OF THE FIGURES

FIG. 1A illustrates the derivation of the constructs employed in the preparation of PDAPP and PDAPP (D664A) transgenic mice.

FIG. 1B illustrates the detection of soluble Aβ in various test animals.

FIG. 1C summarizes the number of Aβ plaques in various test animals.

FIG. 1D illustrates a stained brain section from a 16-month-old PDAPP(D664A) mouse, revealing the presence of Aβ plaques.

FIG. 1E illustrates the cleavage of APP at Asp664 in vivo. An antibody specific for the neo-epitope generated by cleavage of APP at Asp664 6 was used to demonstrate an increase in cleavage in PDAPP in comparison to both controls and PDAPP(D664A) mice.

FIG. 2A summarizes the quantitation of pre-synaptic densities in various test animals.

FIG. 2B summarizes total hippocampal and subfield volumes, as determined by three-dimensional reconstruction using Imaris3D (Bitplane AG, Switzerland) (see FIG. 2C) and confirmed by Cavalieri analysis.

FIG. 2C presents orthogonal, saggital and coronal views of 3D surface reconstructions of the dentate gyral molecular layer of representative PDAPP (red) and B21 (yellow) transgenic mice.

FIG. 3A presents several extracellularly recorded field EPSPs, which were used to assess the strength of basal synaptic transmission between hippocampal CA3 and CA1 cells of 3-7 month-old heterozygous Tg and non-Tg PDAPPJ20 and PDAPP(D664A)B21 mice. Representative field EPSPs at increasing stimulus strength are shown for non-transgenic and transgenic mice as indicated. Note the large input (see inset with expanded time scale: arrow indicates fiber volley, an indirect measure of the number of axons activated) needed to elicit a relatively small EPSP in the PDAPPJ20 Tg mice.

FIG. 3B presents the initial EPSP slopes divided by the amplitude of the fiber volley for Tg and non-Tg animals as indicated (data normalized to non-Tg littermates). Each data point represents average results from 17-22 slices obtained from 6-7 mice. Statistical analysis (ANOVA) revealed a significant group effect (p<0.0005). Post-hoc Tukey tests confirmed that PDAPPJ20 mice had significantly lower basal synaptic transmission than all other groups (p<0.01), while no other group was significantly different from another.

FIG. 3C presents paired-pulse facilitation, expressed as a ratio of average amplitudes of fEPSPs evoked by a pair of stimuli. Data are shown in the figure as average+/−SEM.

FIG. 4A illustrates BrdU labeling of proliferating cells in subgranular zone of hippocampal dentate gyrus. Twelve month control (non-Tg), PDAPP and PDAPP(D664A) mice were given intraperitoneal BrdU for 3 days and sacrificed 1 week later. Cells labeled by BrdU (black dots) were detected by immunohistochemistry. Images shown are representative of 4-6 animals per group.

Figure 4:
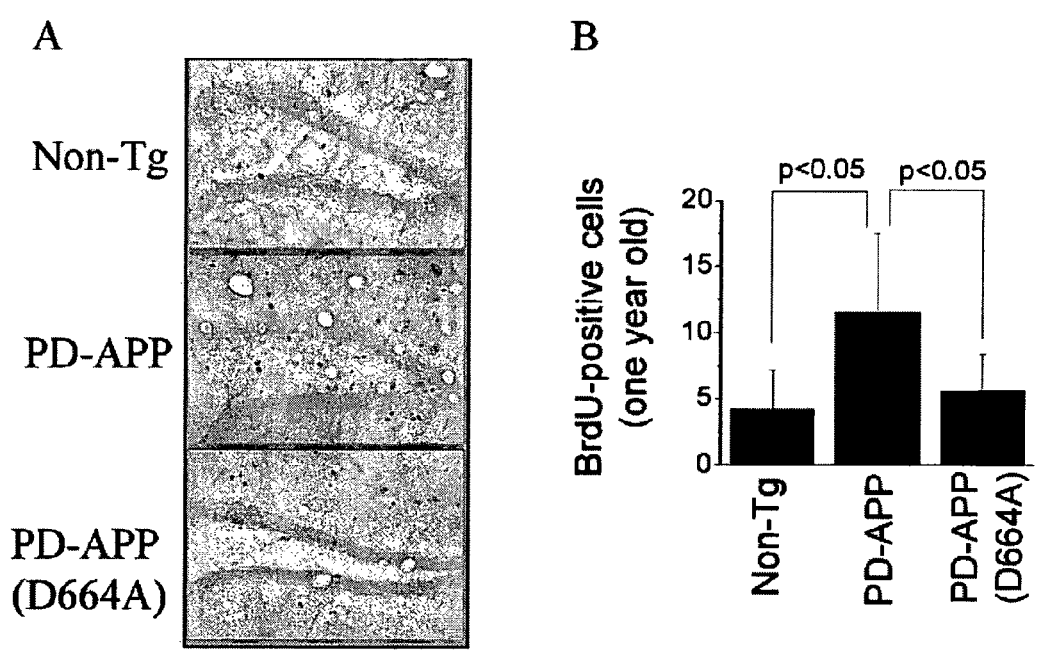
FIG. 4 collectively illustrates the effect of D664A mutation on PDAPP-induced enhancement of hippocampal neurogenesis.

FIG. 4B illustrates the quantitation of BrdU labeling. Data shown are mean cell counts±SD (n=4-6); Student's t test was used to assess the significance of differences.

Figure 5:
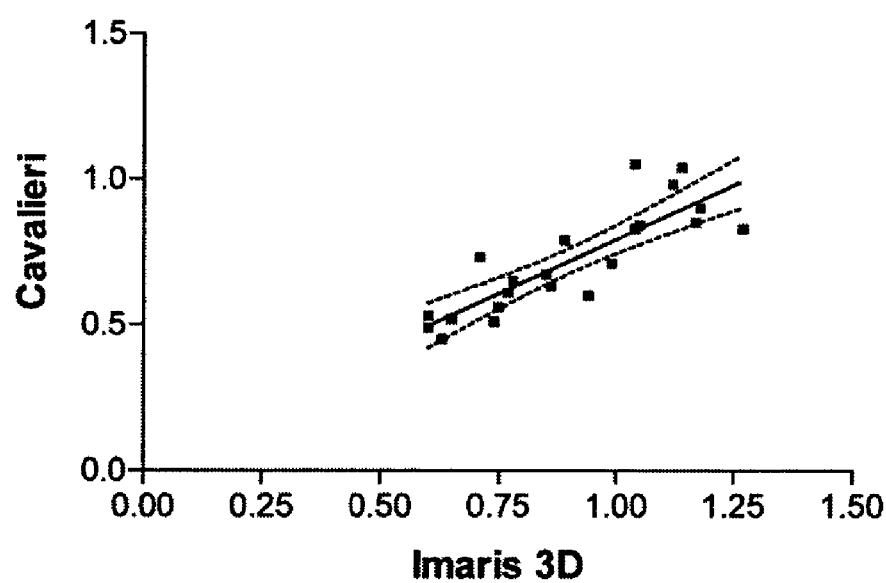

FIG. 5 provides a correlation between volumes derived by Cavalieri analysis and by three-dimensional reconstructions.

DETAILED DESCRIPTION OF THE INVENTION

In accordance with the present invention, there are provided non-human transgenic animals comprising nucleotide sequence encoding a mutant human β-amyloid precursor protein (APP) or APP-like protein, wherein the mutant human APP or APP-like protein comprises a mutation which renders the mutant human APP or APP-like protein resistant to cleavage at Asp664, and wherein the nucleotide sequence encoding the mutant human APP or APP-like protein is operably associated with a suitable promoter.

In one aspect of the invention, cleavage at Asp664 is protease-induced. In a presently preferred aspect of the invention, cleavage at Asp664 is caspase-induced.

In an aspect of the invention, mutant human APP or APP-like proteins comprise a mutation at residue 664. Those of skill in the art recognize that virtually any residue at position 664, other than the native Asp, will reduce the ability of proteases such as caspase from cleaving APP or APP-like protein at position 664. Presently preferred mutations at position 664 include conversion of the native Asp to Ala, Glu, Gln, or the like.

In another aspect of the invention, mutant human APP or APP-like proteins comprise one or more mutations adjacent to residue 664, thereby reducing the ability of proteases such as caspase from cleaving APP or APP-like protein at position 664.

As readily recognized by those of skill in the art, promoters employed in the generation of transgenic animals according to the present invention can be either constitutively active or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, and lacZ promoters of *E. coli*, the α-amylase and the $\sigma^{28}$-specific promoters of *B. subtilis*, the promoters of the bacteriophages of *Bacillus, Streptomyces* promoters, the int promoter of bacteriophage lambda, the bla promoter of the β-lactamase gene of pBR322, and the CAT promoter of the chloramphenicol acetyl transferase gene. Prokaryotic promoters are reviewed by Glick, J. Ind. Microbiol. 1:277 (1987); Watson et al., MOLECULAR BIOLOGY OF THE GENE, 4th Ed., Benjamin Cummins (1987); Ausubel et al., supra, and Sambrook et al., supra.

Promoter regions vary in length and sequence, and can further encompass one or more DNA-binding sites for sequence-specific DNA binding proteins, and/or an enhancer or silencer. Exemplary promoters include the CMV promoter, or a P5 promoter as a promoter for regulating a gene or coding sequence of interest. Such promoters, as well as mutations thereof, are known and have been described in the art (see, e.g., Hennighausen et al., EMBO J., 5, 1367-1371 (1986); Lehner et al., J. Clin. Microbiol., 29, 2494-2502 (1991); Lang et al., Nucleic Acids Res., 20, 3287-95 (1992); Srivastava et al., J. Virol., 45, 555-564 (1983); Green et al., J. Virol., 36, 79-92 (1980); Kyostio et al., supra). Other promoters, however, can also be employed, such as the Ad2 or Ad5 major late promoter and tripartite leader, the Rous sarcoma virus (RSV) long terminal repeat, and other constitutive promoters such as have been described in the literature. For instance, the herpes thymidine kinase promoter (Wagner et al., Proc. Natl. Acad. Sci., 78, 144-145 (1981)), the regulatory sequences of the metallothionine gene (Brinster et al., Nature, 296, 39-42 (1982)) promoter elements from yeast or other fungi such as the Gal 4 promoter, the alcohol dehydrogenase promoter, the phosphoglycerol kinase promoter, and the alkaline phosphatase promoter can be employed. Similarly, promoters isolated from the genome of mammalian cells or from viruses that grow in these cells (e.g., Ad, SV40, CMV, and the like) can be used. Additional promoters contemplated for use herein include the actin promoter, PDGF-β promoter, PrP (neuron-specific) promoter, neuron-specific enolase promoter, and the like.

Instead of using a constitutive promoter, the promoter also preferably can be up- and/or down-regulated in response to appropriate signals. For instance, an inducible promoter, such as the IL-8 promoter, which is responsive to TNF or another cytokine can be employed. Other examples of suitable inducible promoter systems include, but are not limited to, the metallothionine inducible promoter system, the bacterial lac expression system, and the T7 polymerase system. Further, promoters that are selectively activated at different developmental stages (e.g., globin genes are differentially transcribed in embryos and adults) can be employed. In particular, a promoter that can be regulated by exogenous factors such as tetracycline, natural hormones such as the insect-derived hormone, ecdysone (or synthetic variants thereof) or synthetic hormone such as RU486 can be employed. These promoters (and accompanying regulatory factors that similarly can be provided to the cell) have all been described in the art (see, e.g., Delort et al., Human Gene Therapy 7, 809-820 (1996); Clontech, CLONTECHniques, "Tet-Off.™ and Tet-On.™ Gene Expression Systems and Cell Lines", Volume XI, No. 3, 2-5 (July 1996)).

Another option is to use a tissue-specific promoter (i.e., a promoter that is preferentially activated in a given tissue and results in expression of a gene product in the tissue where activated), such as the hepatocyte-specific promoter for albumin or alantitrypsin (Frain et al., Mol. Cell. Biol. 10: 991-999 (1990); Ciliberto et al., Cell 41: 531-540 (1985); Pinkert et al., Genes and Devel., 1, 268-276 (1987); Kelsey et al, Genes and Devel., 1, 161-171 (1987)), the elastase I gene control region which is active in pancreatic acinar cells (e.g., Swift et al., Cell, 38, 639-646 (1984); MacDonald, Hepatology, 7, 425-515 (1987)), the insulin gene control region which is active in pancreatic beta cells (Hanahan, Nature, 315, 115-122 (1985)), the mouse mammary tumor virus control region which is active in testicular, breast, lymphoid and mast cells (Leder et al., Cell, 45, 485-495 (1986)), the myelin basic protein gene control region which is active in oligodendrocyte cells in the brain (Readhead et al., Cell, 48, 703-712 (1987)), and the gonadotropic releasing hormone gene control region which is active in the hypothalamus (Mason et al., Science, 234, 1372-1378 (1986)). Similarly, a tumor-specific promoter, such as the carcinoembryonic antigen for colon carcinoma (Schrewe et al., Mol. Cell Biol. 10: 2738-2748 (1990)) can be used in the vector. According to the invention, any promoter can be altered by mutagenesis, so long as it has the desired binding capability and promoter strength.

As readily recognized by those of skill in the art, a wide variety of non-human animals can be employed for the preparation of invention transgenic animals, including rodents, rabbits, swine, and the like. Presently preferred transgenic animals according to the invention are rodents (e.g., mice, rats, and the like), with mice being especially preferred.

Figure 1:
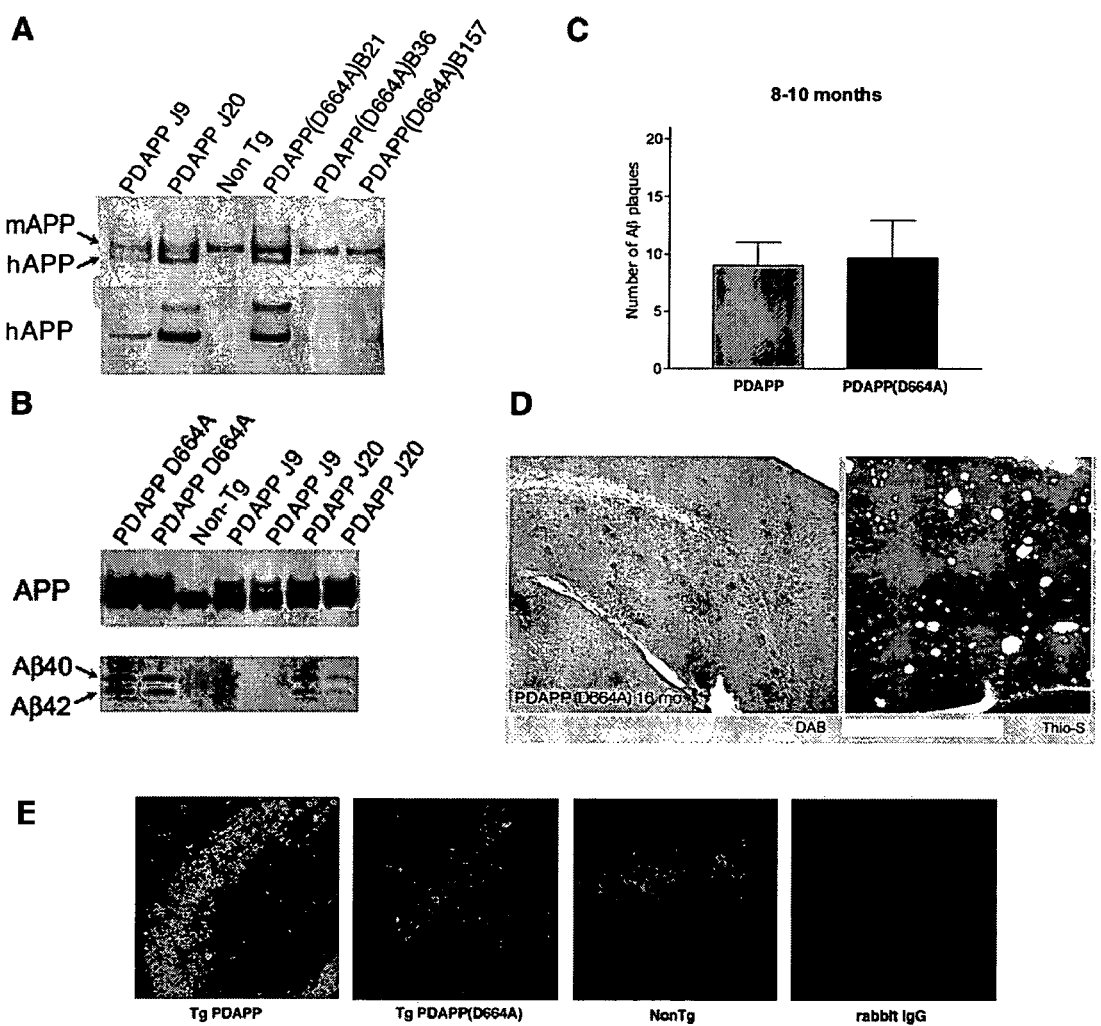
FIG. 1 collectively is directed to the characterization of PDAPP and PDAPP (D664A) transgenic mice.

The D664A mutation, which does not affect Aβ production in cultured cells (see Soriano, S., Lu, D. C., Chandra, S., Pietrzik, C. U. and Koo, E. H. in J Biol Chem 276:29045-50 (2001)), was introduced into a human APP (hAPP) minigene carrying the Swedish (K670N, M671L) and Indiana (V717F) familial AD mutations downstream from the PDGF β-chain promoter. These animals were crossed onto the C57BL/6 background for five to ten generations, and compared to PDAPP transgenic mice with a similar genetic background (J9 and J20 lines (see Hsia et al, and Mucke, supra). Of six transgenic lines generated, one line (PDAPP (D664A) B21) demonstrated APP expression, Aβ concentration, and fibrillar Aβ plaque number that were all similar to those of the PDAPP J20 line (see FIGS. 1A-1D). A second PDAPP(D664A) transgenic line, PDAPP(D664A) B157, showed levels of APP expression moderately lower than those of the PDAPP J9 line (see FIG. 1A). These transgenic lines were selected for further study.

To evaluate whether mutation of Asp664 effectively blocks C-terminal cleavage of hAPP in vivo, brain sections of 3 month-old PDAPP and PDAPP(D664A) mice were immunostained with an antibody that specifically recognizes the C-terminal neo-epitope generated after cleavage of APP at Asp664 (APPNeo; see Galvan, V. et al. in J Neurochem 82:283-94 (2002)). While strong APPNeo immunoreactivity was detected in cell bodies and projections of hippocampal neurons in PDAPP animals, the levels of immunoreactivity present in sections from PDAPP(D664A) animals was indistinguishable from that observed in non-transgenic littermates of either transgenic line (see FIG. 1E).

Figure 2:
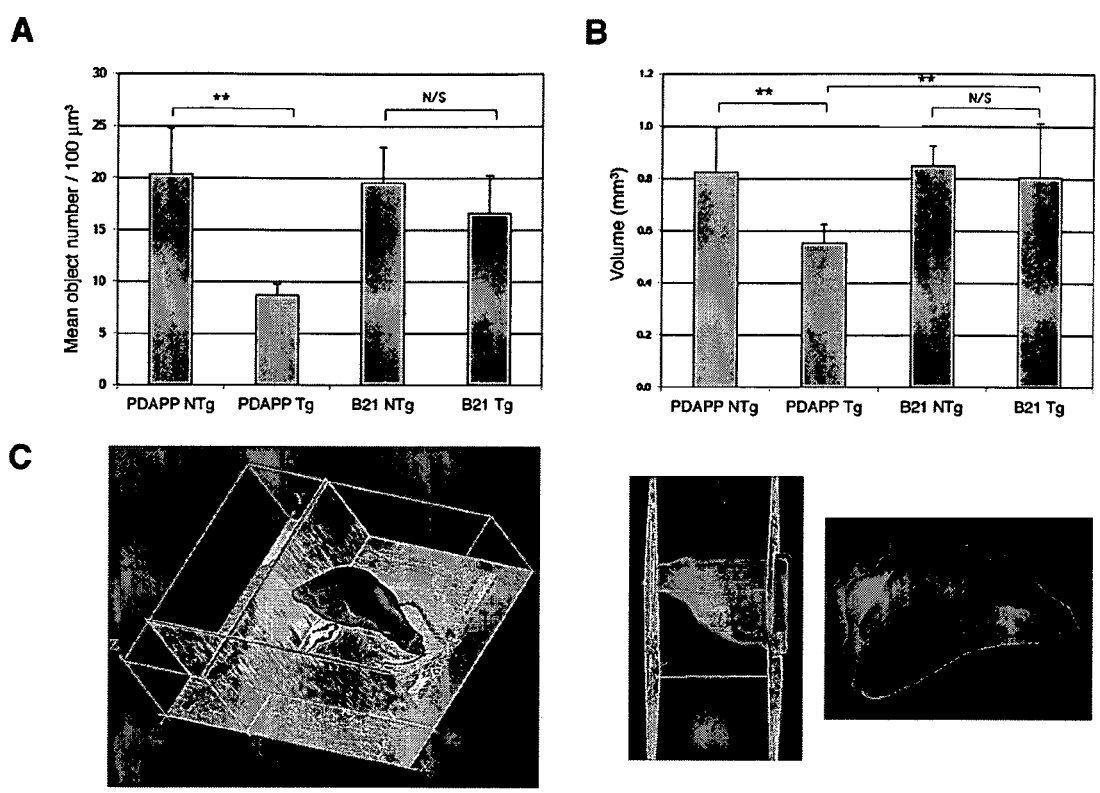
FIG. 2 collectively illustrates the effect of D664A mutation on synaptic loss and dentate gyral atrophy.

The degree of cognitive decline in AD patients correlates strongly with changes in the levels of the presynaptic vesicle protein synaptophysin in the hippocampus and prefrontal cortex (see, for example, Terry, R. D. et al. in Ann Neurol 30:572-80 (1991)). Low levels of synaptophysin, presumably associated with synaptic injury, are associated with the earliest stages of AD (see, for example, Masliah, E. et al. in Neurology 56:127-9 (2001)). PDAPP mice show decreased numbers of hippocampal synaptophysin-immunoreactive presynaptic densities well before plaque formation (see, for example, Hsia, A. Y. et al. in Proc Natl Acad Sci USA 96:3228-33 (1999)). To determine whether the D664A mutation has a role in the loss of presynaptic elements in hippocampi of hAPP transgenic mice, hippocampal presynaptic densities, synaptic densities and dentate gyral volumes were determined in PDAPP, PDAPP(D664A) and control mice at 8-10 mo by a modification of the 'stereological dissector' method (see Example 6 and Hsia, A. Y. et al. in *Proc Natl Acad Sci USA* 96:3228-33 (1999)), since these parameters represent correlates of cognitive decline in Alzheimer's disease. Surprisingly, whereas the PDAPP mice displayed a marked reduction in hippocampal synaptic densities in comparison to their non-transgenic littermates, B21 mice did not (see FIGS. 2A and 2B). A second PDAPP(D664A) transgenic line, B157, yielded identical results.

Similarly, as described recently (see Redwine, J. M., Kosofsky, B., Jacobs, R. E., Games, D., Reilly, J. F., Morrison, J. H., Young, W. G. and Bloom, F. E. in Proc Natl Acad Sci USA 100:1381-6 (2003)), PDAPP mice showed reduced dentate gyral volumes, especially in the molecular layer; however, no significant loss was observed in the B21 mice (see FIG. 2C).

A pronounced decrease in cortical volume is one of the essential neuropathological features of AD. Although not all transgenic mouse models of AD recapitulate this particular feature of the disease, it has been shown that PDAPP mice display reduced dentate gyral volumes at relatively early ages (3-4 months), especially in the molecular layer (see, for example Dodart, J. C. et al. in Neurobiol Dis 7:71-85 (2000) and Redwine, J. M. et al. in Proc Natl Acad Sci USA 100: 1381-6 (2003)). It was, therefore, of interest to determine dentate gyral volumes in PDAPP, PDAPP(D664A), and control animals at 3 months of age by digital three-dimensional reconstruction of Nissl-stained sections, and by manual Cavalieri analysis. Significant dentate gyral shrinkage was observed in brains of PDAPP, but not PDAPP(D664A) mice, both when measured by manual Cavalieri analysis (see FIG. 2B) as well as by digital 3D reconstruction (see FIGS. 2C and 2D). Volumes derived by Cavalieri analysis and by digital three-dimensional reconstructions were highly correlated ($r^2$=0.72, p<0.00001, n=25) (see FIG. 5).

Figure 3:
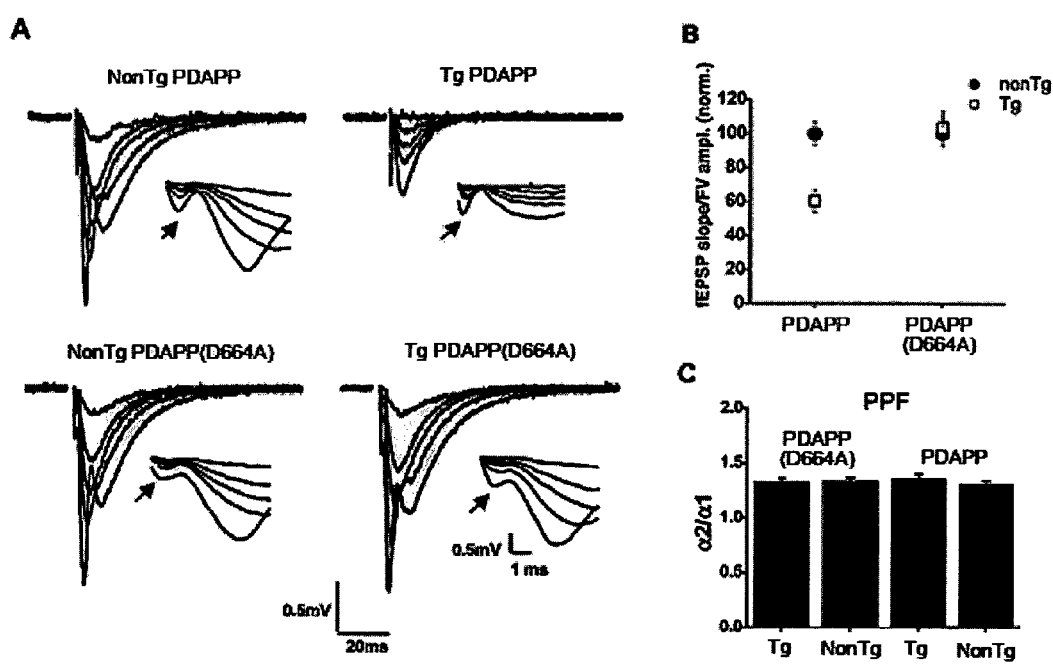
FIG. 3 collectively illustrates the effect of D664A mutation on basal synaptic transmission.

In considering synaptic integrity in APP transgenic mice, functional examination of synaptic transmission is of interest because histological determinations of synaptic numbers may overestimate the number of functional synapses present in the brain. That the loss of presynaptic structures in PDAPP mice is accompanied by an impairment in basal synaptic transmission has been shown (see Hsia, A. Y. et al. in *Proc Natl Acad Sci USA* 96:3228-33 (1999)). To determine whether the restoration of presynaptic densities observed in hippocampi of PDAPP(D664A) mice corresponded to a rescue in synaptic function, electrophysiological recordings were performed on acute hippocampal slices from 3-7 mo PDAPP, PDAPP(D664A,) and control mouse brains. Extracellularly recorded excitatory postsynaptic potentials (fEPSPs) were used to assess the strength of basal synaptic transmission between hippocampal CA3 and CA1 cells. As has been similarly reported with other transgenic APP lines, a ~40% decrease in the basal synaptic transmission (input-output ratio) was observed with PDAPP mice, indicating a significant impairment in synaptic transmission. In contrast, no significant difference was observed in synaptic transmission between PDAPP(D664A) and nontransgenic littermate control mice (see FIGS. 3A and 3B). Consistent with the observed losses in presynaptic density numbers, electrophysiological deficits apparent in PDAPP mice were not present in animals carrying the D664A mutation. Additionally, paired-pulse facilitation, which correlates inversely with probability of transmitter release, was unchanged between all groups examined (see FIG. 3C) suggesting that PDAPP (D664A) mice, like PDAPP transgenic lines, have no additional defects on presynaptic function. Thus, it is likely that the presynaptic elements preserved in PDAPP(D664A) mice represent functional synapses.

Neurogenesis is increased in the hippocampus of patients with AD (see Jin, K. et al. in Proc Natl Acad Sci USA 101: 343-7 (2004)) and in the brains of PDAPP mice. Thus, injury-induced neurogenesis may contribute to brain repair in acute and chronic neurological diseases. To assess the effect of the D664A mutation on PDAPP-induced hippocampal neurogenesis, bromodeoxyuridine (BrdU) was used to label proliferating cells in the subgranular zone of the dentate gyrus (a major site of both normal adult and AD-induced neurogenesis), in 12 mo control, PDAPP and PDAPP(D664A) mice. The number of BrdU-labeled cells (most of which expressed the immature neuronal marker protein, doublecortin) was increased to approximately twice control levels in PDAPP mice, but this effect was abolished by the D664A mutation (see FIG. 4).

In summary, the B21 mice produced Aβ and amyloid deposits indistinguishably from the PDAPP mice, yet they did not display the characteristic loss of hippocampal synaptic density or dentate gyral volume seen in PDAPP animals. These findings suggest that the cleavage of hAPP at Asp664 by caspases (or possibly by a non-caspase protease or proteases) contributes to synaptic loss and dentate gyral volume reduction in hAPP transgenic mice. These observations argue that hippocampal synaptic loss and dentate atrophy in this mouse model of AD are mediated by APP cleavage at Asp664, either independent of Aβ deposition or downstream from Aβ production (see Lu et al., "Amyloid β-protein toxicity is mediated by the formation of amyloid-β protein precursor complexes" in Annals of Neurology, in press). Furthermore, the results indicate that the intracytoplasmic domain of APP plays a key role in these manifestations of the Alzheimer's phenotype.

In addition, the results presented herein demonstrate that APP transgenic mice carrying a mutation at the caspase cleavage site Asp->Ala (D664A) that prevents cleavage of hAPP at Asp664 in vivo continue to produce Aβ and show plaque deposition, yet do not demonstrate the hippocampal synaptic loss or brain shrinkage that characterize the phenotype of PDAPP mice (PDAPP mice show a profound decrease in synaptic transmission). Work with the invention transgenic mice indicates that the synaptic transmission impairment of PDAPP mice is fully restored in PDAPP(D664A) mice.

These results demonstrate that the C-terminal cleavage of APP contributes to the synaptic impairment and volumetric loss observed in a mouse model of AD and are consistent with the C-terminal cleavage of APP being involved in the pathogenesis of AD. Most importantly, the results presented herein constitute genetic experimental evidence indicating that synaptic loss and hippocampal shrinkage can be independent of the production and deposition of Aβ⁻.

Cleavage of the C-terminal portion of APP is likely to affect several different cellular functions in which APP is involved. Invention transgenic animals provide a unique opportunity to examine the early processes that affect synapse loss and underlie the early steps in the pathogenesis of neurodegenerative diseases such as AD. Recovery of synaptic function in the early stages of AD is a far more straightforward undertaking than the replacement of lost neuronal networks at later stages in the progression of the disease. The observations set forth herein with PDAPP(D664A) mice are consistent with the existence of mechanisms not directly associated with the production or deposition of Aβ that are crucial for the AD-associated pathology in mice and constitute novel potential targets for drug discovery. The continued elucidation of the mechanisms operating at the early stages of AD, as provided herein, facilitate the development of therapies that retard, and potentially stop, or even reverse, the synaptic deterioration that occurs in early AD.

The identification of markers associated with a given pathological condition in humans is significantly complicated by the contribution of genotypic, phenotypic and life-history related factors. On the other hand, while transgenic animal models provide adequate experimental systems in which these variables can be controlled, they have a potentially significant drawback, i.e., the potential emergence of physiological responses or activation of compensatory mechanisms as a result of the expression of the transgene during development. Thus, the comparison of transgenic animals to their non-transgenic littermates may yield information about changes that result from the expression of the transgene per se, and not from the pathogenesis of the modeled disease.

Fundamental features of the AD-associated phenotype in PDAPP mice have effectively been reversed in invention transgenic animals by preventing the cleavage of the C-terminus of the hAPP transgene. Since PDAPP and PDAPP (D664A) mice share many genetic similarities, i.e., 1) they are generated from vectors identical but for a A->C transversion, 2) they share the same genetic background, and 3) they express the human APP transgene to comparable levels, one would expect that changes arising from the expression of the transgene per se should be alike in PDAPP and PDAPP (D664A) animals. Thus, the comparison of changes (markers) present in PDAPP mice, but not present in PDAPP (D664A) mice, relative to non-transgenic littermates, allows one to unambiguously identify markers associated with the development of AD and their distinction from those arisen from the expression of the transgene per se, in the absence of confusing genotypic, phenotypic or environmental variables (as animals are fully congenic and can readily be bred and housed in a controlled environment).

Hemizygous transgenic animals from the PDAPP and PDAPP(D664A) line can be generated to be used as experimental animals. Specifically, twelve 2 month-old hemizygous transgenic PDAPP and PDAPP(D664A) animals congenic in the C57BL/6J background, plus 12 non-transgenic littermates, can be generated to produce pooled sera, brain extracts, or extracts of other organs of interest.

The above-described animals can then be used to generate samples, by suitable means, to be used in proteomic or genomic studies. Identification of proteins or mRNAs present in samples from transgenic and non-transgenic animals and the analysis of the data to determine which proteins are uniquely present, absent, increased or decreased in abundance in one of the above-described populations can be carried out using standard techniques, such as, for example, mass spectrometry, DNA microarray hybridization techniques, and the like.

In accordance with a further aspect of the present invention, there are provided methods for identifying compounds useful for the treatment of neurodegenerative diseases, said methods comprising identifying compounds which block the ability of caspase(s) to cleave β-amyloid precursor protein (APP) to produce the carboxyterminal peptide, APP-C31.

As readily recognized by those of skill in the art, compounds which block the ability of caspase(s) to cleave β-amyloid precursor protein (APP) to produce the carboxyterminal peptide, APP-C31, can be identified in a variety of ways, e.g., by contacting APP or APP-like protein with test compound in the presence of caspase, and monitoring the formation of APP-P31, wherein failure of caspase to induce production of APP-P31 is indicative of a compound which is useful for the treatment of neurodegenerative diseases.

Alternatively, compounds which block the ability of caspase(s) to cleave β-amyloid precursor protein (APP) to produce the carboxyterminal peptide, APP-C31, can be identified by contacting APP or APP-like proteins (e.g., APLP1 or APLP2) with test compound in the presence of caspase, and screening for evidence of cleavage selected from the group consisting of translocation of the cleavage product, induction of cell death, induction of atrophy, and induction of synapse loss. APLP1 and APLP2 are members of the APP family of proteins, collectively "APP-like proteins". However, the sites required for γ and β-secretase cleavage of APP are not conserved in either APLP1 or APLP2. These molecules therefore do not have the capacity to generate β-amyloid-like peptides. However, the C-terminal caspase cleavage site that allows for the generation of APP-C31 is conserved in both APLP1 and APLP2. For APLP1, the P4-P1' positions would be VEVDP, and for APLP2, the P4-P1' positions would be VEVDP while in APP, the P4-P1' positions are VEVDA. These sequences, like those in APP, fit well with previously described caspase cleavage sites for the initiator/apical caspases such as caspase-8 and caspase-9. The predicted APLP1-C31 peptide is 52% identical and 77% similar to the APP-C31 peptide, and the predicted APLP2-C31 peptide is 71% identical and 83% similar to the APP-C31 peptide.

As another alternative, cells expressing APP, APLP1, APLP2, or the like, can be screened, in the presence or absence of insult (e.g., Aβ, ischemia, heat shock, hypoxia, glucose deprivation, staurosporine, and the like), for compounds that block the production of APP-C31 (the latter of which can be assayed by using an antibody that specifically detects the carboxyterminal cleavage product of APP, or by alternative methods such as reporter assay, ELISA assay, and the like).

Compounds identified in the above-described screening methods can then be tested in vivo, e.g., by testing the efficacy thereof in an animal model of Alzheimer's disease (i.e., same transgenic without the Asp664->Ala mutation), and comparing the response to that of an invention Asp664->Ala mutant transgenic animal.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including peptides, saccharides, fatty acids, steroids, purines, pyrimidines, derivatives, structural analogs or combinations thereof, and the like.

In accordance with a further aspect of the present invention, there are provided methods for treating neurodegenerative diseases, said methods comprising administering an effective amount of one or more compounds identified by the above-described methods to a subject in need thereof.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

Essentially, any disease that is etiologically linked to the formation and/or deposition of amyloid is contemplated for treatment according to the present invention. As used herein, "neurodegenerative disease" refers to a disorder such as Alzheimer's disease, systemic senile amyloidosis, prion disease, scrapie, bovine spongiform encephalopathy, Creutzfeldt-Jakob disease, Gerstmann-Straussler-Scheinker syndrome, type II diabetes, adult onset diabetes, insulinoma, amyloid A amyloidosis, AL amyloidosis, familial amyloid polyneuropathy (Portuguese, Japanese and Swedish types), familial transthyretin amyloidosis, familial Mediterranean Fever, familial amyloid nephropathy with urticaria and deafness (Muckle-Wells syndrome), hereditary non-neuropathic systemic amyloidosis (familial amyloid polyneuropathy III), familial amyloidosis of Finnish type, familial amyloid cardiomyopathy (Danish type), isolated cardiac amyloid, isolated atrial amyloidosis, idiopathic (primary) amyloidosis, myeloma or macroglobulinemia-associated amyloidosis, primary localized cutaneous nodular amyloidosis associated with Sjogren's syndrome, reactive (secondary) amyloidosis, hereditary cerebral hemorrhage with amyloidosis of Icelandic type, amyloidosis associated with long term hemodialysis, fibrinogen-associated hereditary renal amyloidosis, amyloidosis associated with medullary carcinoma of the thyroid, lysozyme-associated hereditary systemic amyloidosis, and the like.

Amyloid deposits are found in subjects diagnosed with Alzheimer's disease, a neurodegenerative disease characterized by atrophy of nerve cells in the cerebral cortex, subcortical areas, and hippocampus and the presence of plaques, dystrophic neurites and neurofibrillary tangles. In Alzheimer's disease, dystrophic or aberrant neurite growth, synapse loss, and neurofibrillary tangle formation are strong correlates of disease severity. Dystrophic neurons characteristically contain abundant electrodense multilaminar bodies in the cytoplasm of the neurites and have disruption of synaptic junctions. The dystrophic neurons surround deposits of amyloid, thereby forming the senile plaques located throughout the brain neuropil as well as in the walls of cerebral blood vessels. Invention methods for treating Alzheimer's disease can reduce or block the atrophy of nerve cells, reduce or block the formation of senile plaques or neurofibrillary tangles, and the like, such that the development of the disease is slowed or arrested.

Amyloid deposits are also found in the islets of Langerhans in patients diagnosed with type II diabetes. The deposits contain an amyloid protein that is derived from a larger precursor called islet amyloid polypeptide (IAPP) or amylin which, in normal animals, has a hormonal role. IAPP is produced by the beta cells of the islets and has a profound effect on glucose uptake by the liver and striated muscle cells. In transgenic mice having a transgene for human amylin and which are fed a high fat diet, overproduction of amylin leads to islet amyloid deposition (see Pathology, 3rd ed. (1999) supra, p. 1226). Invention methods for treating amyloid deposits in the islets of Langerhans in patients having type II diabetes can reduce or prevent the formation of amyloid protein, reduce or prevent the deposition of amyloid protein into amyloid deposits, and the like.

Yet another disease where amyloid deposits are noted is prion disease, one type of spongiform encephalopathy. Prion diseases are neurodegenerative conditions characterized clinically by progressive ataxia and dementia, and pathologically by vacuolization of spongiform brain tissue. Amyloid deposits are associated with at least one prion disease known as kuru. In kuru, about 70% of prion protein accumulates extracellulary to form plaques, in contrast to normal prion protein which is a constitutively expressed cell-surface glycoprotein (see Pathology, 3.sup.rd ed. supra, pp. 1492-1496). Invention methods for treating prion disease can reduce or prevent the production of amyloid protein, reduce or prevent the deposition of amyloid plaques, and the like.

Still another disease where amyloid deposits are noted is amyloid A amyloidosis. Amyloid A amyloidoses refer to amyloidoses from seemingly unrelated disorders such as chronic inflammatory disorders, neoplastic disorders, and hereditary disorders. The deposition of amyloid protein is secondary to the underlying disease condition. The precursor molecule is serum amyloid A (SAA), an acute phase reactant, which can be used as a surrogate marker of inflammation in many diseases. Invention methods for treating amyloid A amyloidosis can reduce or prevent the production of amyloid protein, reduce or prevent the production of the precursor to amyloid protein, prevent or reduce any one of several steps necessary to generate an active amyloid protein, reduce or prevent the deposition of amyloid plaques, and the like.

Yet another disease where amyloid deposits are noted is familial transthyretin amyloidosis which is the most common form of Familial Amyloidotic Polyneuropathy (FAP). The human amyloid disorders, familial amyloid polyneuropathy, familial amyloid cardiomyopathy and senile systemic amyloidosis, are caused by insoluble transthyretin (TTR) fibrils, which deposit in the peripheral nerves and heart tissue. Transthyretin is a homotetrameric plasma protein implicated in the transport of thyroxine and retinol. The most common amyloidogenic TTR variant is V30M-TTR, while L55P-TTR is the variant associated with the most aggressive form of FAP. Invention methods for treating amyloidoses caused by transthyretin can reduce or prevent the production of amyloid protein, reduce or prevent the production of the precursor to amyloid protein, prevent or reduce any one of several steps necessary to generate an active amyloid protein, reduce or prevent the deposition of amyloid plaques, and the like.

A further disease where amyloid deposits are noted is AL amyloidosis. AL amyloidosis is a class of diseases related to a primary disorder of immunoglobulin production which includes primary amyloidosis, plasma cell dyscrasia, immunoblastic lymphoma, multiple myeloma, and the like. Primary systemic AL (amyloid light-chain) amyloidosis is a plasma cell disorder in which depositions of amyloid light-chain protein cause progressive organ failure. The prognosis of primary amyloidosis is generally poor, with a median survival of 1-2 years. The precursor protein is an immunoglobulin light chain in both localized and systemic AL-amyloidosis which shows the same pattern of fragmentation and changes of primary structure. Invention methods for treating amyloidoses caused by AL amyloid proteins can reduce or prevent the production of amyloid protein, reduce or prevent the production of the precursor to amyloid protein, prevent or reduce any one of several steps necessary to generate an active amyloid protein, reduce or prevent the deposition of amyloid plaques, and the like.

As used herein, "administering" refers to providing a therapeutically effective amount of a compound to a subject, using oral, sublingual, intravenous, subcutaneous, transcutaneous, intramuscular, intracutaneous, intrathecal, epidural, intraocular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

The preferred route of administration will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound employed per administration event without the weight of carrier (when carrier is used).

Targeted-delivery systems, such as polymer matrices, liposomes, and microspheres can increase the effective concentration of a therapeutic agent at the site where the therapeutic agent is needed and decrease undesired effects of the therapeutic agent. With more efficient delivery of a therapeutic agent, systemic concentrations of the agent are reduced because lesser amounts of the therapeutic agent can be administered while accruing the same or better therapeutic results. Methodologies applicable to increased delivery efficiency of therapeutic agents typically focus on attaching a targeting moiety to the therapeutic agent or to a carrier which is subsequently loaded with a therapeutic agent.

Various drug delivery systems have been designed by using carriers such as proteins, peptides, polysaccharides, synthetic polymers, colloidal particles (i.e., liposomes, vesicles or micelles), microemulsions, microspheres and nanoparticles. These carriers, which contain entrapped pharmaceutically useful agents, are intended to achieve controlled cell-specific or tissue-specific drug release.

The compounds contemplated for use herein can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The compounds described herein, when in liposome form can contain, in addition to the compounds described herein, stabilizers, preservatives, excipients, and the like. The preferred lipids are the phospholipids and the phosphatidyl cholines (lecithins), both natural and synthetic. Methods to form liposomes are known in the art. (See, e.g., Prescott, Ed., Methods in Cell Biology, Volume XIV, Academic Press, New York, N.Y., (1976), p 33 et seq.)

Several delivery approaches can be used to deliver therapeutic agents to the brain by circumventing the blood-brain barrier. Such approaches utilize intrathecal injections, surgical implants (Ommaya, Cancer Drug Delivery, 1: 169-178 (1984) and U.S. Pat. No. 5,222,982), interstitial infusion (Bobo et al., Proc. Natl. Acad. Sci. U.S.A., 91: 2076-2080 (1994)), and the like. These strategies deliver an agent to the CNS by direct administration into the cerebrospinal fluid (CSF) or into the brain parenchyma (ECF).

Drug delivery to the central nervous system through the cerebrospinal fluid is achieved, for example, by means of a subdurally implantable device named after its inventor the "Ommaya reservoir". The drug is injected into the device and subsequently released into the cerebrospinal fluid surrounding the brain. It can be directed toward specific areas of exposed brain tissue which then adsorb the drug. This adsorption is limited since the drug does not travel freely. A modified device, whereby the reservoir is implanted in the abdominal cavity and the injected drug is transported by cerebrospinal fluid (taken from and returned to the spine) to the ventricular space of the brain, is used for agent administration. Through omega-3 derivatization, site-specific biomolecular complexes can overcome the limited adsorption and movement of therapeutic agents through brain tissue.

Another strategy to improve agent delivery to the CNS is by increasing the agent absorption (adsorption and transport) through the blood-brain barrier and the uptake of therapeutic agent by the cells (Broadwell, Acta Neuropathol., 79: 117-128 (1989); Pardridge et al., J. Pharmacol. Experim. Therapeutics, 255: 893-899 (1990); Banks et al., Progress in Brain Research, 91:139-148 (1992); Pardridge, Fuel Homeostasis and the Nervous System, ed.: Vranic et al., Plenum Press, New York, 43-53 (1991)). The passage of agents through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier, or by its covalent coupling to a peptide vector capable of transporting the agent through the blood-brain barrier. Peptide transport vectors are also known as blood-brain barrier permeabilizer compounds (U.S. Pat. No. 5,268,164). Site specific macromolecules with lipophilic characteristics useful for delivery to the brain are described in U.S. Pat. No. 6,005,004.

Other examples (U.S. Pat. Nos. 4,701,521, and 4,847,240) describe a method of covalently bonding an agent to a cationic macromolecular carrier which enters into the cells at relatively higher rates. These patents teach enhancement in cellular uptake of bio-molecules into the cells when covalently bonded to cationic resins.

U.S. Pat. No. 4,046,722 discloses anti-cancer drugs covalently bonded to cationic polymers for the purpose of directing them to cells bearing specific antigens. The polymeric carriers have molecular weights of about 5,000 to 500,000. Such polymeric carriers can be employed to deliver compounds described herein in a targeted manner.

Further work involving covalent bonding of an agent to a cationic polymer through an acid-sensitive intermediate (also known as a spacer) molecule, is described in U.S. Pat. Nos. 4,631,190 and 5,144,011. Various spacer molecules, such as cis-aconitic acid, are covalently linked to the agent and to the polymeric carrier. They control the release of the agent from the macromolecular carrier when subjected to a mild increase in acidity, such as probably occurs within a lysosome of the cell. The drug can be selectively hydrolyzed from the molecular conjugate and released in the cell in its unmodified and active form. Molecular conjugates are transported to lysosomes, where they are metabolized under the action of lysosomal enzymes at a substantially more acidic pH than other compartments or fluids within a cell or body. The pH of a lysosome is shown to be about 4.8, while during the initial stage of the conjugate digestion, the pH is possibly as low as 3.8.

As employed herein, the phrase "therapeutically effective amount", when used in reference to compounds contemplated for use in the practice of the present invention, refers to a dose of compound sufficient to provide circulating concentrations high enough to impart a beneficial effect on the recipient thereof. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. Dosage levels typically fall in the range of about 0.001 up to 100 mg/kg/day; with levels in the range of about 0.05 up to 10 mg/kg/day being preferred.

As used herein, the phrase "contacting" refers to providing compounds to cells or cellular targets. Contacting may take place in solid, liquid or gaseous phase, and refers to events that take place extracellularly and intracellularly. Those of skill in the art will recognize that providing compounds to cells in vivo may be accomplished by numerous modes of administration, including oral, sublingual, intravenous, subcutaneous, transcutaneous, intramuscular, intracutaneous, intrathecal, epidural, intraoccular, intracranial, inhalation, rectal, vaginal, and the like.

In accordance with yet another aspect of the present invention, there are provided methods for treating neurodegenerative diseases, said method comprising blocking the ability of protease(s) to cleave β-amyloid precursor protein (APP) and/or APP-like proteins (e.g., APLP1 or APLP2) to produce the carboxyterminal peptide, APP-C31.

As readily recognized by those of skill in the art, the ability of protease(s) to cleave APP and/or Aβ can be blocked in a variety of ways, e.g., by anti-protease antibodies, antisense nucleotides based on protease coding sequence, peptides, peptidomimetics, ribozymes, interfering RNAs, protease antagonists, small molecules which block the ability of proteases to cleave the intracytoplasmic region of APP and/or Aβ, and the like.

For example, expression, including over-expression, of a mutant APP according to the present invention can be inhibited by administration of an antisense molecule that binds to and inhibits expression of the mRNA encoding the polypeptide. Alternatively, expression can be inhibited in an analogous manner using a ribozyme that cleaves the mRNA. General methods of using antisense and ribozyme technology to control gene expression, or of gene therapy methods for expression of an exogenous gene in this manner are well known in the art. Each of these methods utilizes a system, such as a vector, encoding either an antisense or ribozyme transcript of a mutant APP according to the present invention.

The term "ribozyme" refers to an RNA structure of one or more RNAs having catalytic properties. Ribozymes generally exhibit endonuclease, ligase or polymerase activity. Ribozymes are structural RNA molecules which mediate a number of RNA self-cleavage reactions. Various types of trans-acting ribozymes, including "hammerhead" and "hairpin" types, which have different secondary structures, have been identified. A variety of ribozymes have been characterized. See, for example, U.S. Pat. Nos. 5,246,921, 5,225,347, 5,225,337 and 5,149,796. Mixed ribozymes comprising deoxyribo and ribooligonucleotides with catalytic activity have been described. Perreault, et al., *Nature,* 344:565-567 (1990).

As used herein, "antisense" refers of nucleic acid molecules or their derivatives which specifically hybridize, e.g., bind, under cellular conditions, with the genomic DNA and/or cellular mRNA encoding a mutant APP according to the present invention, so as to inhibit expression of that protein, for example, by inhibiting transcription and/or translation. The binding may be by conventional base pair complementarity, or, for example, in the case of binding to DNA duplexes, through specific interactions in the major groove of the double helix.

In one aspect, the antisense construct is an nucleic acid which is generated ex vivo and that, when introduced into the cell, can inhibit gene expression by, without limitation, hybridizing with the mRNA and/or genomic sequences of an APP or APP-like molecule.

Antisense approaches can involve the design of oligonucleotides (either DNA or RNA) that are complementary to APP or APP-like mRNA. The antisense oligonucleotides will bind to the APP or APP-like mRNA transcripts and prevent translation.

Although absolute complementarity is preferred, it is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

General methods of using antisense, ribozyme technology and RNAi technology, to control gene expression, or of gene therapy methods for expression of an exogenous gene in this manner are well known in the art. Each of these methods utilizes a system, such as a vector, encoding either an antisense or ribozyme transcript of an APP or APP-like polypeptide. The term "RNAi" stands for RNA interference. This term is understood in the art to encompass technology using RNA molecules that can silence genes. See, for example, McManus, et al. *Nature Reviews Genetics* 3:737 (2002). In this application, the term "RNAi" encompasses molecules such as short interfering RNA (siRNA), microRNAs (miRNA), small temporal RNA (stRNA). Generally speaking, RNA interference results from the interaction of double-stranded RNA with genes.

In general, oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R. (1994) Nature 372:333). Antisense oligonucleotides complementary to mRNA coding regions are less efficient inhibitors of translation but could be used in accordance with the invention. Whether designed to hybridize to the 5', 3' or coding region of APP or APP-like polypeptide mRNA, antisense nucleic acids should be at least six nucleotides in length, and are preferably less than about 100 and more preferably less than about 50 or 30 nucleotides in length. Typically they should be between 10 and 25 nucleotides in length. Such principles will inform the practitioner in selecting the appropriate oligonucleotides In preferred embodiments, the antisense sequence is selected from an oligonucleotide sequence that comprises, consists of, or consists essentially of about 10-30, and more preferably 15-25, contiguous nucleotide bases of a nucleic acid sequence encoding APP or APP-like polypeptide.

Using such sequences, antisense oligonucleotides can be designed. Such antisense oligonucleotides would be administered to cells expressing APP or APP-like polypeptide and the levels of the target RNA or protein with that of an internal control RNA or protein would be compared. Results obtained using the antisense oligonucleotide would also be compared with those obtained using a suitable control oligonucleotide. A preferred control oligonucleotide is an oligonucleotide of approximately the same length as the test oligonucleotide. Those antisense oligonucleotides resulting in a reduction in levels of target RNA or protein would be selected.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. U.S.A.* 86:6553-6556; Lemaitre et al. (1987) *Proc. Natl. Acad. Sci. USA* 84:648-652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al. (1988) BioTechniques 6:958-976) or intercalating agents. (See, e.g, Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from moieties such as 5-fluorouracil, 5-bromouracil, 5-chlorouracil, 5-iodouracil, hypoxanthine, xanthine, 4-acetylcytosine, and 5-(carboxyhydroxyethyl) uracil. The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. (see also U.S. Pat. Nos. 5,176,996; 5,264,564; and 5,256,775).

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) *Nucl. Acids Res.* 15:6625-6641). The oligonucleotide is a 2'-0-methylribonucleotide (Inoue et al. (1987) *Nucl. Acids Res.* 15:6131-6148), or a chimeric RNA-DNA analogue (Inoue et al. (1987) FEBS Lett. 215:327-330).

Also suitable are peptidyl nucleic acids, which are polypeptides such as polyserine, polythreonine, etc. including copolymers containing various amino acids, which are substituted at side-chain positions with nucleic acids (T,A,G, C,U). Chains of such polymers are able to hybridize through complementary bases in the same manner as natural DNA/ RNA. Alternatively, an antisense construct of the present invention can be delivered, for example, as an expression plasmid or vector that, when transcribed in the cell, produces RNA complementary to at least a unique portion of the cellular mRNA which encodes a kinase polypeptide of the invention.

While antisense nucleotides complementary to APP or APP-like polypeptide coding region sequence can be used, those complementary to the transcribed untranslated region are most preferred.

In accordance with still another aspect of the present invention, there are provided methods for preventing hippocampal synaptic loss, said methods comprising blocking the ability of caspase(s) or other proteases to cleave β-amyloid precursor protein (APP) and/or APP-like proteins (e.g., APLP1 or APLP2).

As noted above, the ability of protease(s) to cleave APP and/or APP-like proteins (e.g., APLP1 or APLP2) can be blocked in a variety of ways, e.g., by anti-protease antibodies, antisense nucleotides based on protease coding sequence, peptides, peptidomimetics, ribozymes, interfering RNAs, protease antagonists, small molecules which block the ability of proteases to cleave the intracytoplasmic region of APP and/or APP-like proteins (e.g., APLP1 or APLP2), and the like.

In accordance with a further aspect of the present invention, there are provided methods for preventing dentate gyral atrophy, said methods comprising blocking the ability of caspase(s) or other proteases to cleave β-amyloid precursor protein (APP) and/or APP-like proteins (e.g., APLP1 or APLP2).

As noted above, the ability of protease(s) to cleave APP and/or APP-like proteins (e.g., APLP1 or APLP2) can be blocked in a variety of ways, e.g., by anti-protease antibodies, antisense nucleotides based on protease coding sequence, peptides, peptidomimetics, ribozymes, interfering RNAs, protease antagonists, small molecules which block the ability of proteases to cleave the intracytoplasmic region of APP and/or Aβ, and the like.

In accordance with yet another aspect of the present invention, there are provided gene therapy methods for treating neurodegenerative diseases, said methods comprising introducing a mutation into β-amyloid precursor protein (APP) so as to prevent caspase mediated cleavage thereof.

Indeed, advances have resulted in practical approaches to human gene therapy that have demonstrated positive initial results (reviewed in Miller, *Nature* 357:455-460, 1992). The basic science of gene therapy is described in Mulligan (*Science* 260:926-931, 1993).

Thus, in one embodiment, an expression vector containing a mutant APP coding sequence is inserted into cells, the cells are grown in vitro and then infused in large numbers into patients.

Gene therapy according to the present invention may involve the use of an adenovirus containing mutant APP cDNA targeted to neural cells, systemic expression of mutant APP by implantation of engineered cells, injection with mutant APP-encoding virus, injection of naked mutant APP DNA into appropriate tissues, and the like.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding mutant APP according to the invention into the targeted cell population (e.g., neural cells). Methods which are well known to those skilled in the art can be used to construct recombinant viral vectors containing coding sequences (Maniatis et al., Molecular Cloning: A Laboratory Manual, Cold Spring Harbor Laboratory, N.Y., 1989; Ausubel et al., Current Proto-cols in Molecular Biology, Greene Publishing Associates and Wiley Interscience, N.Y., 1989). Alter-natively, recombinant nucleic acid molecules encoding protein sequences can be used as naked DNA or in a recon-stituted system e.g., liposomes or other lipid systems for delivery to target cells (e.g., Felgner et al., *Nature* 337: 387-8, 1989). Several other methods for the direct transfer of plasmid DNA into cells exist for use in human gene therapy and involve targeting the DNA to receptors on cells by complexing the plasmid DNA to proteins (Miller, supra).

In its simplest form, gene transfer can be performed by simply injecting minute amounts of DNA into the nucleus of a cell, through a process of microinjection (Capecchi, *Cell* 22:479-88, 1980). Once recombinant genes are introduced into a cell, they can be recognized by the cell's normal machinery for transcription and translation, and a gene product will be expressed. Other methods have also been attempted for introducing DNA into larger numbers of cells. These methods include: transfection, wherein DNA is precipitated with calcium phosphate and taken into cells by pinocytosis (Chen et al., *Mol. Cell Biol.* 7:2745-52, 1987); electroporation, wherein cells are exposed to large voltage pulses to introduce holes into the membrane (Chu et al., *Nucleic Acids Res.* 15:1311-26, 1987); lipofection/liposome fusion, wherein DNA is packaged into lipophilic vesicles which fuse with a target cell (Felgner et al., *Proc. Natl. Acad. Sci. USA*. 84:7413-7417, 1987); and particle bombardment using DNA bound to small projectiles (Yang et al., *Proc. Natl. Acad. Sci.* 87:9568-9572, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene (Curiel et al., *Am. J. Respir. Cell. Mol. Biol.*, 6:247-52, 1992).

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a mutant APP is provided in which the nucleic acid sequence is expressed only in specific tissue. Methods of achieving tissue-specific gene expression are set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

The invention will now be described in greater detail with reference to the following non-limiting examples.

EXAMPLE 1

Generation of PDAPP (D664A) Mutation

A G to C point mutation was introduced into the PDGF β-chain promoter-driven hAPP minigene carrying the Swedish and Indiana mutations (see Hsia et al, supra) that changed Asp664 (APP695 numbering) to Ala (PDAPP(D664A)). The mutation was confirmed by sequencing and by allele-specific amplification.

EXAMPLE 2

Generation of Transgenic Mice

Microinjection of the PDAPP(D664A) transgene, identification of transgenic founders by PCR, and selection of the PDAPP(D664) B21 line for use in the present study were carried out as previously described (see Li, Y., Carlson, E., Murakami, K., Copin, J. C., Luche, R., Chen, S. F., Epstein, C. J. and Chan, P. H. in J Neurosci Methods 89, 49-55 (1999)), which proceeded substantially as follows.

A 2 ng/µl solution of linear purified human PDAPP (D664A) transgene DNA free of vector sequences was microinjected into the male pronucleus of 1-day old B6D2F1/J eggs and transferred into pseudopregnant CD1 foster mothers 24 h later. Identification of founders was done by PCR using primers specific for the hAPP transgene:

```
GGTGAGTTTGTAAGTGATGCC,      (SEQ ID NO:1)
and

TCTTCTTCTTCCACCTCAGC,       (SEQ ID NO:2)
``` and primers specific for the mouse PKR gene:

```
CAGGCCACTGGGAGGAAAAATG,     (SEQ ID NO:3)
and

ACCTTCTGTCATGTGGAGGTCC.     (SEQ ID NO:4)
```

Transgenic lines were maintained by heterozygous crosses with C57BL/6J breeders (Charles River Laboratories). All transgenic animals were heterozygous with respect to the transgene, and non-transgenic littermates were used as controls. Human and mouse APP were detected in brain homogenates by immunoprecipitation followed by Western blotting using the anti-APP 5A3/1G7 monoclonal antibody (see Soriano et al, supra).

EXAMPLE 3

Detection of Soluble Aβ

Aβ levels in brain were assessed from CHAPS soluble lysates by immunoprecipitation followed by Western blotting with the 26D6 anti-APP monoclonal antibody that recognizes residues 1-12 of the Aβ peptide. The immunoprecipitates were fractionated on bicine-urea SDS-PAGE gels to fractionate the Aβ 40 and 42 species (see Weggen, et al, in Nature 414:212-6 (2001)). APP was immunoblotted from CHAPS brain lysates with CT15, a polyclonal antibody recognizing the C-terminus of APP. All the animals were age-matched, between 3-4 months of age, prior to deposition of aggregated Aβ peptides.

EXAMPLE 4

Quantitation of Aβ Deposits

Fifty-micron vibratome brain sections of heterozygous PDAPP and PDAPP(D664A) B21 mice were stained with 3D6 antibody as previously described (see Wyss-Coray, T., Masliah, E., Mallory, M., McConlogue, L., Johnson-Wood, K., Lin, C. and Mucke, L. in Nature 389:603-6 (1997). Total hippocampal Aβ plaques were identified and counted by investigators blinded with respect to strain and genotype. Data are expressed as mean+/−SD.

EXAMPLE 5

Cleavage of APP at Asp664 In Vivo

An antibody specific for the neo-epitope generated by cleavage of APP at Asp664 (see Galvan et al., in J Neurochem 82:283-94 (2002)) was used to demonstrate an increase in cleavage in the PDAPP mice in comparison to both the controls and the PDAPP(D664A).

EXAMPLE 6

Quantitation of Presynaptic Densities

To determine the integrity of presynaptic terminals, 50 µm vibratome sections from brains of heterozygous female PDAPP and PDAPP(D664A) mice were stained with α-synaptophysin antibodies (10 µg/ml, Chemicon) followed by fluorescein isothiocyanate-conjugated donkey anti-mouse IgG (1:400, Vector Laboratories), counterstained with propidium iodide, and imaged with a laser scanning confocal microscope (Nikon PCM-2000) using a 100× objective and a 2.7× digital zoom. Three-dimensional numerical densities (expressed as number of objects per mm3) of synaptophysin-immunoreactive presynaptic terminals in CA1 stratum radiatum were determined by a modification of the stereological dissector method [4]

For each animal, six 1024×1024 pixel (45 µm×45 µm) monochrome confocal images were obtained at 2070 PMT gain. An additional set of six paired confocal images were captured at the same x and y coordinates but in a plane 0.9 µm below the plane of acquisition of the first confocal image (z=−0.90 µm) at 2100 PMT gain to correct for photobleaching using Simple PCI software (Compix, Inc.). To reduce the variability introduced in the measurements by variations in the proportion of unstained regions corresponding to neuronal processes in each field, two 10 µm×10 µm subfields were collected from the brightest area of each pair of images, avoiding areas occupied by processes. Each image in the pair of 10 µm×10 µm subfields at different z coordinates were pseudocolored red and green, and superimposed. The resulting images were corrected for blur using Photoshop and the number of immunolabelled objects traversing both planes (yellow) was counted using Simple PCI. Object counts obtained from 12 such dissectors spaced randomly through six serial hippocampal sections per mouse (avoiding overlap between dissectors) were averaged for each subject and used for subsequent statistical analyses (see FIGS. 2B and 2C).

EXAMPLE 7

Volume Determinations

Hippocampal dentate gyrus (DG) and molecular layer (ML) were defined with the aid of an appropriate atlas (see Paxinos, G., Franklin K. B. J. "The Mouse Brain in Stereotaxic Coordinates" Academic Press (2001), San Diego). Total hippocampal and subfield volumes were determined by three-dimensional reconstruction using Imaris3D (Bitplane AG, Switzerland) (see FIG. 2C) and confirmed by Cavalieri analysis (see FIG. 2B).

For volume determinations using Imaris 3D (Bitplane) and manual Cavalieri analysis, the border of each hemi-hippocampus, dentate gyrus (DG) and molecular layer (ML) subfields in a 1-in-4 systematic random series of 2×images of Nissl-stained 40 µm sections of snap-frozen mouse brains (corresponding to twenty-five 100-day heterozygous transgenic males or non-transgenic male littermates) was drawn at the gray/white matter border with the fimbria and corpus callosum, at the border of the molecular layer and the lacunosum moleculare, and the polymorph layer and the thalamus, respectively, with the aid of an appropriate atlas [10]. The subiculum was excluded. In each sample, the last section was defined as the last section showing a continuous tract of corpus callosum fibers. For Imaris 3D volume determinations, the sections were aligned using the Align application (Bitplane) and the resulting series were manually adjusted when necessary. A voxel size of 3.3 μm×3.3 μm×160 μm was used for all subsequent 3D reconstructions and volume measurements. For volume estimation using the Cavalieri principle, a 200 μm grid was overlaid on a 1280×1024 pixel image of each section in the sample, and the number of grid crossings within each hemi-hippocampus, dentate gyrus and molecular layer subfields were counted for each section in the sample. Volumes were calculated as previously described (see Gonzalez-Lima, F., Berndt, J. D., Valla, J. E., Games, D. and Reiman, E. M. in Neuroreport 12, 2375-9 (2001)).

Volumes derived by Cavalieri analysis and Imaris 3D reconstructions were highly correlated ($r^2=0.72$, $p<0.00001$, n=25). No significant difference was found in total body weight or brain weight between strains or genotypes. For all experiments, mice and brain tissue samples were coded to blind investigators with respect to strain and genotype. Data are expressed as mean+/−SD. Significance ($p<0.05$) was determined by Student's t test (assuming equal variance) or the Pearson correlation coefficient test followed by runs test for regression analyses.

EXAMPLE 8

In Vitro Slice Electrophysiology

Horizontal hippocampal slices (400 μm) were made from 3-7 month PDAPPJ20, PDAPP(D664A) B21 and non-transgenic littermate control mice (J20 mice were chosen to compare to B21 since they expressed similar levels of the APP transgene). Slices were prepared using standard methods (see, for example, Contractor, A. et al. in J Neurosci 23:422-9 (2003)). Briefly, animals were anesthetized with isoflurane and decapitated. Brains were removed and sliced under ice-cold sucrose slicing artificial CSF (ACSF) containing: 85 mM NaCl, 2.5 mM KCl, 1.25 mM $NaH_2PO_4$, 25 mM $NaHCO_3$, 25 mM glucose, 75 mM sucrose, 0.5 mM $CaCl_2$, and 4 mM $MgCl_2$, and equilibrated with 95% $O_2$ and 5% $CO_2$ which also contained 10 μM D,L-APV and 100 μM kynurenate. Prior to recoding, slices were incubated at room temperature for at least 1 hour in a standard ACSF containing: 125 mM NaCl, 2.4 mM KCl, 1.2 mM $NaH_2PO_4$, 25 mM $NaHCO_3$, 25 mM glucose, 1 mM $CaCl_2$, and 2 mM $MgCl_2$. During recordings, slices were continuously perfused with ACSF containing 2 mM $CaCl_2$ and 1 mM $MgCl_2$.

Extracellular field potentials (fEPSPs) were recorded in the striatum radiatum of the CA1 region of hippocampus using a glass recording pipette filled with extracellular solution (tip resistance 2-3 MOhm). Evoked fEPSPs were recorded in response to stimulation of the Schaffer collateral/commissural pathway using a concentric bipolar electrode passing constant current. Basal synaptic transmission was measured by comparing the input and output relation of the fEPSPs recorded (Hsia et al); input was the peak amplitude of the fiber volley, the output was the initial slope of the fEPSP. For each animal the fiber volley (FV) amplitude and initial slope of the fEPSP responses to a range of stimulation from 5-800 μA was measured and a response curve generated for both values. The input output relation was then calculated by dividing the slope of the fEPSP by the FV amplitude (from each point along the linear portion on the response curve) and taking the average value. Paired pulse facilitation was elicited using an interstimulus interval of 40 ms and ratio measured as the peak amplitude of fEPSP(2)/fEPSP(1). Results were analyzed using a one-way analysis of variance (ANOVA) followed by Tukey post-hoc tests.

EXAMPLE 9

Neurogenesis

BrdU (50 mg/kg) was dissolved in saline and given i.p., twice daily at 8-hr intervals, for 3 consecutive days, and mice were killed 1 week later. Brain sections were stained with mouse monoclonal anti-BrdU (Roche, 2 μg/ml) and biotinylated goat-anti-mouse IgG (Vector, 1:200) and staining was visualized with diaminobenzidine and $H_2O_2$. BrdU-positive cells in dentate gyrus were counted blindly in 5-7, 50-μm coronal sections per mouse, spaced 200 μm apart. Cells were counted under high-power on a Nikon E800 microscope with Magnifire digital camera, and the image displayed on a computer monitor. Results were expressed as the average number of BrdU-positive cells per section.

While the invention has been described in detail with reference to certain preferred embodiments thereof, it will be understood that modifications and variations are within the spirit and scope of that which is described and claimed.

That which is claimed is:

1. A transgenic mouse whose genome comprises a nucleotide sequence encoding a mutant human β-amyloid protein (APP) operably linked to a neuronal promoter, wherein said mutant APP encodes an FAD mutation further comprising an amino acid substitution of Asp 664 (APP 695 numbering), rendering said mutant APP resistant to cleavage at Asp664, wherein said transgenic mouse produces amyloid plaques but produces no loss of hippocampal synaptic density or dentate gyral volume.

2. The transgenic mouse of claim 1 wherein cleavage at Asp664 is caspase-induced.

3. The transgenic mouse of claim 1 wherein said mutant human APP comprises a mutation at residue 664.

4. The transgenic mouse of claim 3 wherein the mutation at residue 664 changes Asp to Ala, Glu, or Gln.

5. The transgenic mouse of claim 1 wherein said mutant human APP comprises a mutation adjacent to residue 664.

6. The transgenic mouse of claim 1 wherein said promoter is constitutively active.

7. The transgenic mouse of claim 6 wherein said promoter is selected from the group consisting of the actin promoter, PDGF-β promoter, PrP (neuron-specific) promoter, and the neuron-specific enolase promoter.

8. The transgenic mouse of claim 1 wherein said promoter is inducible.

9. The transgenic mouse of claim 8 wherein said promoter is selected from the group consisting of Tet-on, Tet-off, RU486-inducible promoter system, and ecdysone-inducible promoter system.

10. The transgenic mouse of claim 1 wherein the APP is APP.

11. The transgenic mouse of claim 10, wherein said APP comprises Swedish and Indiana familial Alzheimer's Disease mutations.

* * * * *